US010299978B2

(12) United States Patent
Zachar et al.

(10) Patent No.: US 10,299,978 B2
(45) Date of Patent: May 28, 2019

(54) SYSTEM, METHOD AND KIT FOR ORAL CARE

(71) Applicant: Airway Medix S.A., Warsaw (PL)

(72) Inventors: Oron Zachar, Tel Aviv (IL); Yair Ramot, Kfar Maas (IL); Eizik Amar, Ashdod (IL)

(73) Assignee: Airway Medix S.A, Warsaw (PL)

(*) Notice: Subject to any disclaimer, the term of this patent is extended or adjusted under 35 U.S.C. 154(b) by 0 days.

(21) Appl. No.: 15/974,840

(22) Filed: May 9, 2018

(65) Prior Publication Data

US 2018/0256430 A1 Sep. 13, 2018

Related U.S. Application Data

(63) Continuation-in-part of application No. PCT/IB2017/001354, filed on Oct. 2, 2017.
(Continued)

(51) Int. Cl.
*A61G 15/16* (2006.01)
*A61C 17/02* (2006.01)
(Continued)

(52) U.S. Cl.
CPC .......... *A61G 15/16* (2013.01); *A46B 11/0041* (2013.01); *A46B 11/06* (2013.01);
(Continued)

(58) Field of Classification Search
CPC ............ A46B 11/0041; A46B 11/0051; A46B 11/0055; A46B 11/0062; A46B 11/06;
(Continued)

(56) References Cited

U.S. PATENT DOCUMENTS 2,586,930 A * 2/1952 Florence ................. A47B 63/02
116/323
4,466,150 A * 8/1984 Jurt ........................ A46B 15/00
116/308
(Continued)

FOREIGN PATENT DOCUMENTS

EP 0992224 A2 4/2000
EP 1143876 A1 10/2001
(Continued)

OTHER PUBLICATIONS

JP2013-075033 Machine Translation (by EPO and Google) published on Apr. 25, 2013 Kawabata et al.
(Continued)

*Primary Examiner* — Wade Miles
*Assistant Examiner* — Shannel N Wright
(74) *Attorney, Agent, or Firm* — Marc Van Dyke; Fourth Dimension IP

(57) ABSTRACT

A kit comprising a base module, a plurality of rodded oral care devices, a hanger, a support element that hangs from the hanger, and a non-electronic multi-input multi-display counter is disclosed herein. The support element for supporting each rodded oral care device of the plurality of devices. Embodiments relate to fluid loading/unloading mechanism involving elements of the base module. The non-electronic multi-input multi-display counter may be used to track different types of oral care operations, e.g. at least some of which are performed using the base module and/or a rodded oral care device. Related methods are disclosed.

11 Claims, 25 Drawing Sheets

Related U.S. Application Data

(60) Provisional application No. 62/449,093, filed on Jan. 22, 2017, provisional application No. 62/449,101, filed on Jan. 22, 2017, provisional application No. 62/449,021, filed on Jan. 21, 2017, provisional application No. 62/403,151, filed on Oct. 2, 2016, provisional application No. 62/403,150, filed on Oct. 2, 2016, provisional application No. 62/403,156, filed on Oct. 2, 2016, provisional application No. 62/542,188, filed on Aug. 7, 2017.

(51) Int. Cl.
| | |
|---|---|
| *A61C 17/26* | (2006.01) |
| *A61C 19/02* | (2006.01) |
| *A46B 13/08* | (2006.01) |
| *A61C 17/34* | (2006.01) |
| *A46B 11/00* | (2006.01) |
| *A46B 11/06* | (2006.01) |
| *A46B 15/00* | (2006.01) |
| *G06M 1/24* | (2006.01) |

(52) U.S. Cl.
CPC .......... *A46B 13/08* (2013.01); *A46B 15/0053* (2013.01); *A61C 17/0208* (2013.01); *A61C 17/26* (2013.01); *A61C 17/3481* (2013.01); *A61C 19/02* (2013.01); *A46B 2200/1066* (2013.01); *G06M 1/245* (2013.01)

(58) Field of Classification Search
CPC ....... A46B 11/063; A46B 13/08; A46B 13/04; A46B 15/0002; A46B 15/001; A61G 15/16; A61G 15/14; G06M 1/245; A61C 17/02; A61C 17/16; A61C 17/26; A61C 17/3481; A61C 17/227; A61C 17/0208; A61C 3/025; A61C 19/02
USPC .............. 433/89, 77; 235/103; 116/306–324; 40/5
See application file for complete search history.

(56) References Cited

U.S. PATENT DOCUMENTS

| | | |
|---|---|---|
| 5,456,361 A | 10/1995 | Walsh et al. |
| 5,709,866 A | 1/1998 | Booras et al. |
| 6,038,997 A * | 3/2000 | Madden ............... A45C 11/005 116/308 |
| 6,129,547 A | 10/2000 | Cise et al. |
| 6,186,782 B1 | 2/2001 | Luppi |
| 6,238,213 B1 | 5/2001 | Young et al. |
| 6,241,412 B1 | 6/2001 | Spies et al. |
| 6,622,333 B1 | 9/2003 | Rehkemper et al. |
| 6,632,091 B1 | 10/2003 | Cise et al. |
| 6,679,642 B1 | 1/2004 | Dillingham et al. |
| 7,080,980 B2 | 7/2006 | Klupt |
| 7,901,153 B1 | 3/2011 | Strider |
| 8,087,843 B2 | 1/2012 | Ottaviani et al. |
| 8,302,776 B2 | 11/2012 | Lien |
| 8,304,122 B2 | 11/2012 | Poshusta et al. |
| 8,614,023 B2 | 12/2013 | Poshusta et al. |
| 8,668,660 B2 | 3/2014 | Janssen et al. |
| 9,027,192 B1 | 5/2015 | Cole |
| 9,144,298 B2 | 9/2015 | Fattori |
| 9,343,758 B2 | 5/2016 | Poshusta et al. |
| 2008/0166683 A1 | 7/2008 | Liao et al. |
| 2009/0197220 A1 | 8/2009 | Cindrich |
| 2009/0230050 A1 | 9/2009 | Jersey et al. |
| 2010/0203399 A1 | 8/2010 | Poshusta et al. |
| 2011/0070016 A1 | 3/2011 | Richardson |
| 2011/0151404 A1 | 6/2011 | Dombrowski |
| 2011/0214240 A1 | 9/2011 | Jimenez et al. |
| 2013/0040216 A1 | 2/2013 | Poshusta et al. |
| 2013/0149662 A1 | 6/2013 | Meloul-Tzubeli |
| 2013/0298911 A1 | 11/2013 | Wlaschin et al. |
| 2014/0106246 A1 | 4/2014 | Poshusta et al. |
| 2015/0047134 A1 | 2/2015 | Prendergast et al. |
| 2015/0133864 A1 | 5/2015 | Zachar et al. |
| 2015/0190597 A1 | 7/2015 | Zachar et al. |
| 2016/0113384 A1 | 4/2016 | Olson |
| 2016/0121066 A1 | 5/2016 | Zachar et al. |
| 2016/0193439 A1 | 7/2016 | Zachar et al. |
| 2017/0042648 A1 | 2/2017 | Zachar et al. |
| 2017/0071326 A1 | 3/2017 | Wu et al. |
| 2017/0079419 A1 | 3/2017 | Wu et al. |
| 2017/0106160 A1 | 4/2017 | Zachar |
| 2017/0189589 A1 | 7/2017 | Zachar et al. |
| 2017/0215570 A1 | 8/2017 | Wu et al. |
| 2017/0231379 A1 * | 8/2017 | Wu ...................... A46B 11/002 401/282 |
| 2017/0238688 A1 | 8/2017 | Wu et al. |
| 2017/0258217 A1 | 9/2017 | Zachar et al. |
| 2017/0318946 A1 | 11/2017 | Davidson et al. |
| 2017/0326317 A1 | 11/2017 | Zachar |
| 2017/0347790 A1 | 12/2017 | Zachar et al. |
| 2018/0078350 A1 * | 3/2018 | Zachar ................. A61C 17/221 |
| 2018/0084898 A1 | 3/2018 | Vincent et al. |

FOREIGN PATENT DOCUMENTS

| | | | |
|---|---|---|---|
| JP | 2013075033 A | 4/2013 | |
| WO | WO2016185165 A1 | 11/2016 | |
| WO | WO 2017122200 A1 * | 7/2017 | ............... A46B 9/04 |
| WO | WO2018060767 A1 | 4/2018 | |

OTHER PUBLICATIONS

IS1.22 OralCare UK Issue3 Published Apr. 1, 2014.
Sage Product QCare Brochure Published Aug. 1, 2015.
International Search Report for PCT/IB2017/001354, dated Mar. 11, 2018.

* cited by examiner

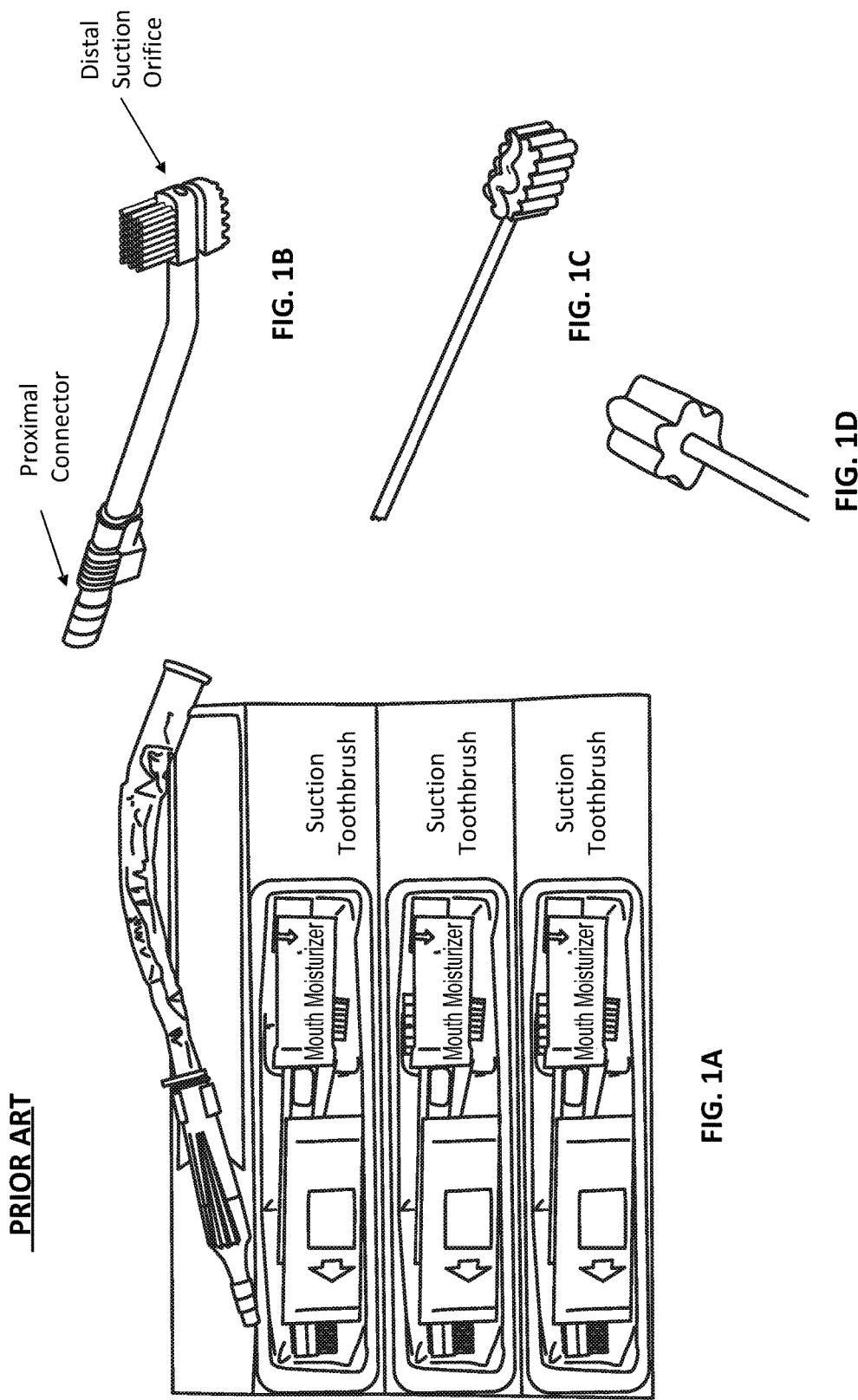

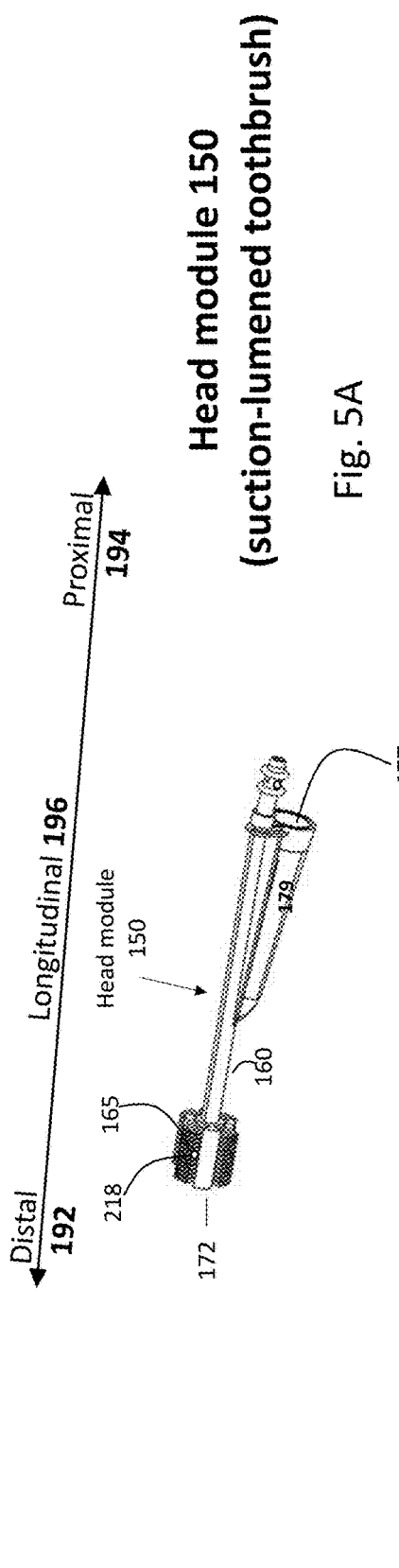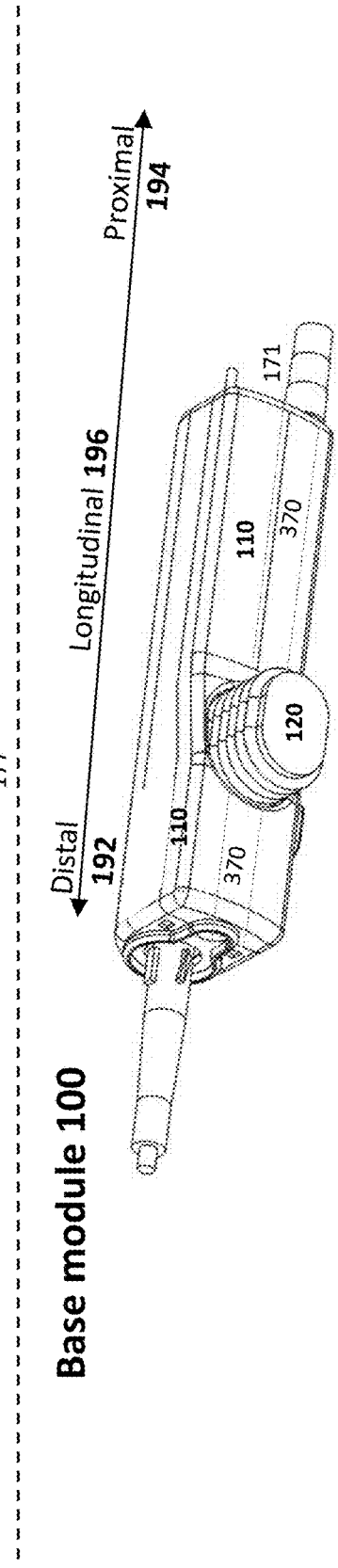
Fig. 5A — Head module 150 (suction-lumened toothbrush)
Fig. 5B — Base module 100

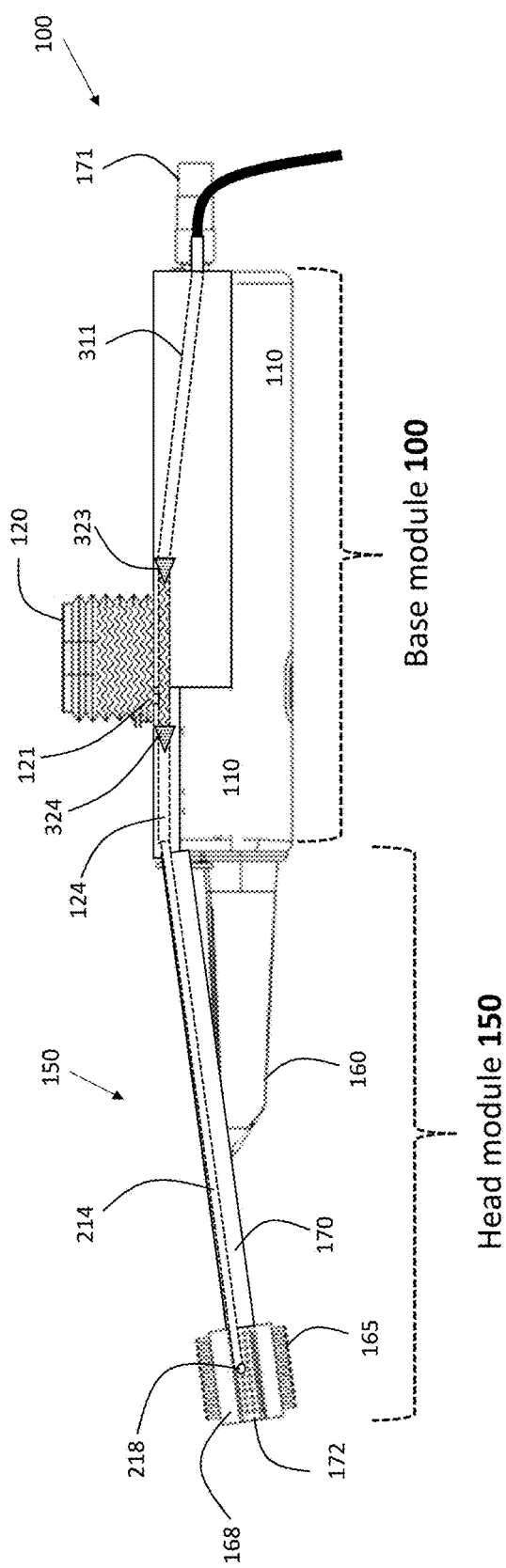

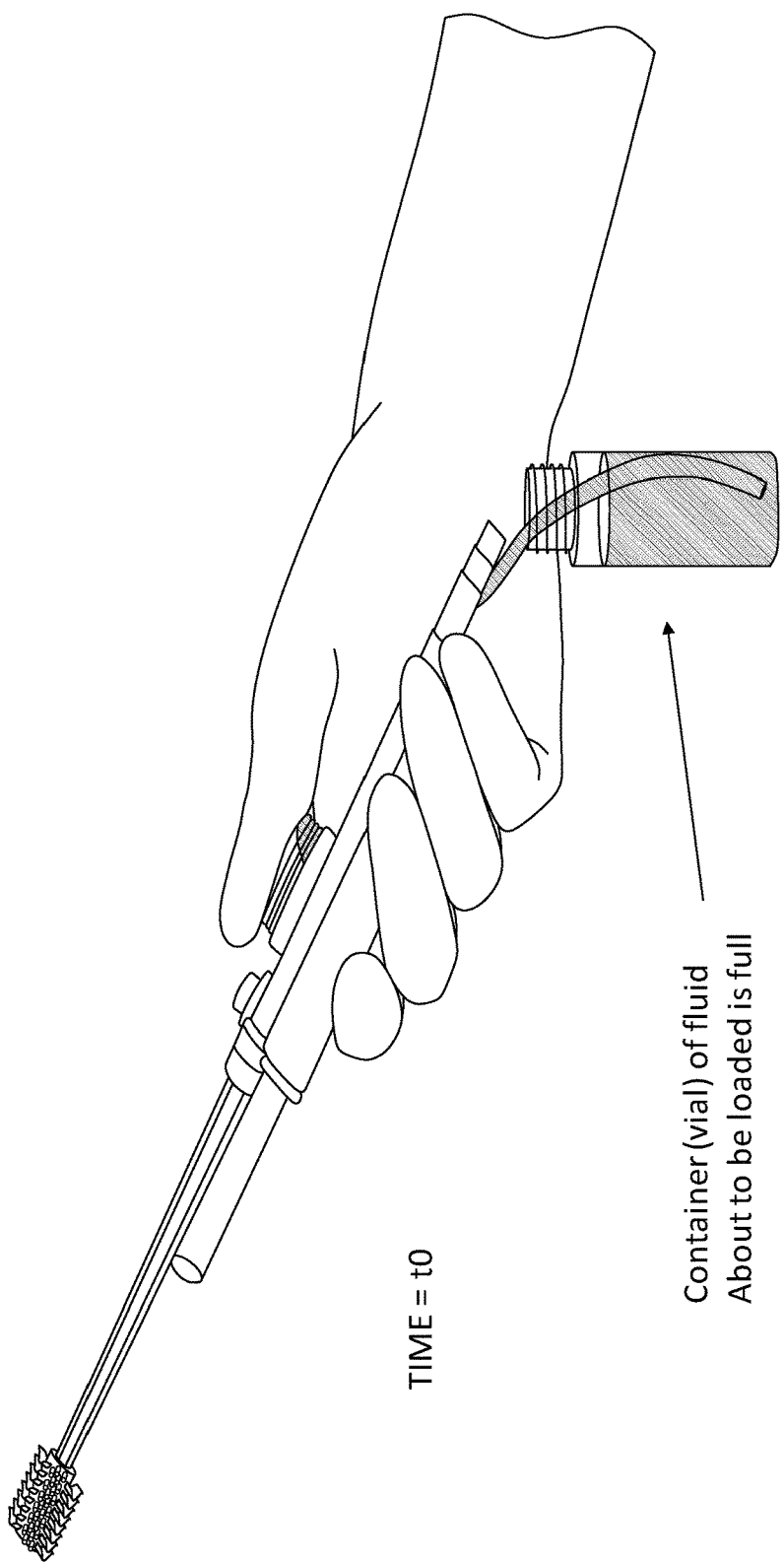

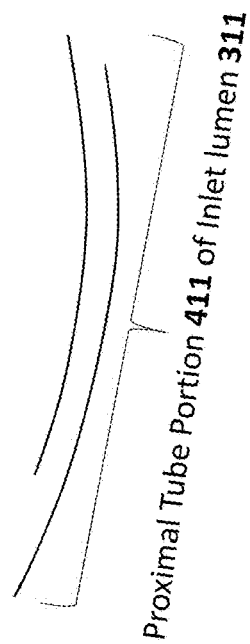
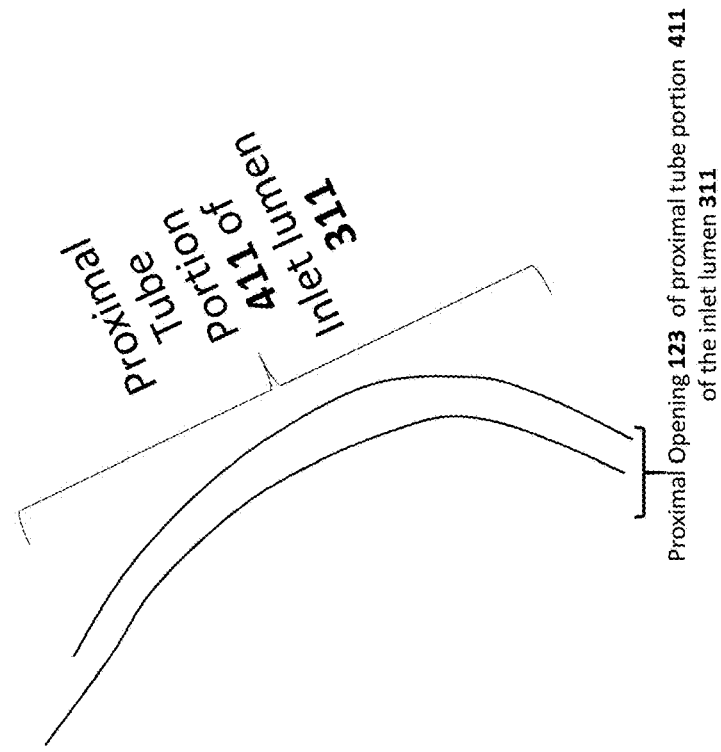
Fig. 11B
Fig. 11A

SYSTEM, METHOD AND KIT FOR ORAL CARE

CROSS-REFERENCE TO RELATED APPLICATIONS

This patent application is a continuation in part of PCT/IB2017/001354 filed on Oct. 2, 2017 which published on as WO/2018/060767 on Apr. 5, 2018, and which is incorporated herein by reference in its entirety.

FIELD OF THE INVENTION

Embodiments of the present invention relate to methods, systems and kits for performing and/or monitoring oral care.

BACKGROUND

Oral Care Kits

Oral care kits for performing a multi-treatment oral care cycle are known in the art. For example, U.S. Pat. No. 7,866,477 discloses an oral care kit comprising a substantially rectangular box having oral care packs positioned therein. Each oral care pack contains oral care devices for administering oral care treatment during a 24 hour oral care treatment cycle. The oral care packs are useful for treating intubated patients in the hospital intensive care unit (ICU).

The fact that each compartment may store a different type of oral care pack allows the user (e.g. a nurse in an ICU) to keep track of the different types of oral-care treatments, and in particular to apply the correct number of treatments in the correct ratio.

United States Patent Publication 20110155612 shows another example of an oral care kit.

An additional prior art example (see FIG. 1A) of an oral care kit is available from Sage Products. This oral care kit comprises a plurality of packs (for example, 3 individual packs that are attached to each other). Each individual pack is sealed. Upon opening of an individual pack, the pack is opened irreversibly and the seal is broken irreversibly.

Within each pack of the prior art oral care kit is both a sponged-rod device (i.e. a rod with a sponge at the end) and a lumened toothbrush-suction hybrid device (used interchangeable with the term 'suction-lumened-toothbrush'). Both sponged-rod devices and suction-lumened brushes are examples of 'rodded oral care devices.'

The devices of FIGS. 1B-1D are all rodded oral care devices; the device of FIG. 1B is suction-lumened-toothbrush.

Prior art oral care kits often include sachets of flowable media as well—for example, sachets of disinfectant or mouth moisturizer (i.e. to be applied to the gums).

As is known in the art, oral care kits typically have multiple packages and each package (e.g. sealed packaged or oral care apparatus between two partitioned) has a pre-determined number of each type of device. To perform an oral care cycle, a caregiver first opens a first packages having a predetermined count of each type of device and uses every oral care device within the first package. Then the caregiver opens a second packages having a predetermined count (i.e. the same count or different counts) of each type of device. And so on.

Because the caregiver will typically use each oral care device sequentially and only for one session, it is possible for manufacturers to help caregivers comply with a specific oral care cycle by including the correct number of each type of oral care device within each individual package.

Suction-Lumened Toothbrushes and Sponged Rod Devices—Examples of Devices Employed for (i) Toothbrushing Sessions and (ii) Soft-Tissue-Lubrication Sessions As noted above, oral care kits (e.g. the kit of FIG. 1A) may include both: (i) suction lumened toothbrush(es); and (ii) sponged rod device(s), where sponge material is mounted to an end of a rod. Both are examples of rodded oral-care devices. As discussed in this section, (i) the suction lumened toothbrush is used (e.g. by nurses) respectively to subject patients (e.g. in ICUs) 'toothbrushing sessions' and (ii) and the sponged rod device are is used (e.g. by nurses) to subject patients (e.g. in ICUs) to 'soft-tissue lubrication sessions.'

Thus, oral care kits (e.g. the kit of FIG. 1A) may include one or more suction lumened toothbrushes. Suction lumened toothbrushes include a suction lumen along the length of the toothbrush and toothbrush bristles at a distal end. Commercially available suction-lumened toothbrushes typically include (i) a proximal connector (e.g. tapered) at the proximal end of the suction lumen and (ii) a distal suction orifice the distal end of the suction lumen. When the proximal connector is connected to a source of negative pressure, matter (e.g. biofilm) is first suctioned into the suction lumen via the distal suction orifice, and then transported through the suction lumen in a proximal direction.

These features of suctioned lumened toothbrushes allow for the caregiver (e.g. a nurse) to simultaneously brush that patient's teeth and suction matter out of our his/her mouth matter. During a 'toothbrushing session,' brushing of the subject's teeth is the dominant mode of operation—optionally, there may be a certain minimal amount of lubrication of soft tissue of the subject's mouth, but the dominant mode of operation during a toothbrushing session is to brush the subject's teeth rather than to lubricate soft-tissue of the patient's mouth rather. Another required feature of toothbrushing sessions is suctioning of matter from the subject's mouth by applying a suction source to a suction lumen so that matter (i.e. driven by negative pressure in the suction lumen and from the suction source) while the subject's teeth are brushed.

As noted above, in addition to suctioned lumened toothbrushes, oral care kits may also include one or more sponged rod devices.

A sponged rod device (i.e. sponge material mounted to an end of a rod) is typically used for 'soft tissue lubrication' operations. A soft tissue lubrication session is performed by a caregiver (e.g. nurse) upon a human subject (e.g. intubated patient in the ICU) and is characterized primarily by lubricating contact between the sponge (e.g. which may hold a cleaning fluid—e.g. comprising a disinfectant) and soft tissue (e.g. lips, gums) of the human subject's mouth—optionally, there may be a certain minimal amount of brushing of the subject's teeth, but the dominant mode of operation during a soft tissue lubrication is to lubricate soft-tissue of the patient's mouth rather than brushing the subject's teeth. Optionally, during soft tissue lubrication sessions matter is suctioned from the subject's mouth.

The term "mouth-moisturizing" session (or operation) is used interchangeably with soft-tissue-lubrication session (or operation) or 'gum-moisturizing' session (or operation) or soft-tissue moisturizing session (or operation).

Concluding Remarks

There is an ongoing need for systems and methods which facilitate oral care in the ICU at a reduced cost and/or in a manner that reduces the amount of space required in the ICU.

The following issued patents and patent publications provide potentially relevant background material, and are all incorporated by reference in their entirety: U.S. Pat. Nos. 6,186,782, 6,766,548, 6,920,659, 8,453,285, US 20110155612 and U.S. Pat. No. 7,866,477. Any feature or combination of features disclosed in any of the aforementioned prior art documents may be combined with any feature disclosed herein.

SUMMARY OF EMBODIMENTS

The following document is incorporated herein by reference in its entirety: PCT/IB2017/001354 filed on Oct. 2, 2017 which published as WO/2018/060767 on Apr. 5, 2018.

Embodiments of the invention relate to an oral care kit which (i) does not rely on packaging to count oral care operations, instead providing a non-electronic multi-input and multi-display counter; and (ii) includes a base module of a multi-module toothbrush device, the base module having a novel fluid loading/delivery mechanism described below.

The kit further includes (i) a plurality of rodded oral care devices, at least one of which is a head module of the multi-module toothbrush device; (ii) a hanger; and (iii) a support element for supporting each of the rodded oral care devices (e.g. which can be 'loaded' onto the shelf or slot or bag).

Both the support element and the non-electronic multi-input and multi-display counter are mechanically coupled to the hanger. When the kit is assembled and in use (e.g. see FIGS. 2 and 7A-7F), the hanger serves two functions: (i) the support element hangs from the hanger, so that the hanger supports the weight of both the support element and the plurality of rodded oral care devices; and (ii) the non-electronic multi-input and multi-display counter is attached to and supported by the hanger.

Thus, the hanger serves as a "common hanger" for both (i) the multi-input and multi-display counter which is used to count oral care operations and (ii) the support element (e.g. shelf or slot or bag) that holds the rodded oral care devices employed in oral care operations tracked using the multi-input and multi-display counter.

As will be discussed below, the head module of the multi-module toothbrush device is a suctioned lumen toothbrush that is detachably attachable to base module. The head and base modules may attached to each other to form the multi-module toothbrush device which may be used to subject an intubated patient to a toothbrushing session. For example, during the toothbrushing session, fluid (i.e. that is pre-loaded into the reservoir of the base module using the novel fluid loading/delivery mechanism) is delivered into the intubated patient's mouth, once again using the novel fluid loading/delivery mechanism.

Toothbrushing sessions are one example of oral care operations that are typically tracked using the presently-disclosed non-electronic multi-input and multi-display counter that is mechanically coupled to the common hanger.

Fluid Loading/Unloading Mechanism (See FIGS. 6A-6D)

The onboard reservoir of the base module is compressible and is in fluid communication with first and second one-way valves arranged in a specific manner relative to the onboard fluid reservoir. Use of the fluid loading/delivery mechanism is now explained according to a non-limiting example, where, a nurse (or other caregiver) holds the base module in the palm of his/her hand, gripping with one or more fingers, and positioning his/her thumb on a surface of the reservoir.

According to this example, loading of the onboard compressive reservoir is performed as follows: after compressing the reservoir by pre-applying pressure to the aforementioned reservoir surface with his/her thumb (e.g. in FIG. 6A), release of this thumb-applied pressure (e.g. in FIG. 6B) causes the compressible reservoir to expand, generating negative pressure within the reservoir. This negative pressure suctions fluid through an inlet lumen, past the first one-way valve and into the reservoir. During the fluid loading, (i) the suctioned fluid enters into the inlet lumen via a proximal opening thereof; and (ii) a presence of the second one-way valve blocks backflow, via a section of the fluid-delivery lumen, into the fluid reservoir.

According to this example, ejection of fluid (see FIG. 6D) from the onboard compressive reservoir is performed as follows: the user simply re-applies pressure to the reservoir surface with his/her thumb, so as to force fluid out of the reservoir, though the fluid-delivery lumen section and into the patient's mouth. This may be performed during a toothbrushing session when the base module is coupled to the suction-lumened toothbrush head module and the tip thereof is disposed within the patient's mouth. The ejected fluid flows through the fluid lumen and past the second one-way valve. During ejection, the first one-way valve prevent fluid from passing back through the inlet lumen towards a proximal opening of the inlet lumen (e.g. the inlet lumen includes an external tube portion and the proximal opening of the inlet lumen corresponds to the proximal opening of the external tube portion).

In this example, the thumb does not need to leave the surface of the reservoir, and movement of the thumb along a single 'vertical' axis perpendicular to the reservoir surface serves both to load fluid into the reservoir and to eject fluid therefrom. The one-way valves prevent unwanted fluid flow from the 'wrong source' during fluid loading (i.e. from head module) and may prevent unwanted fluid flow through the inlet lumen during the ejection stage (e.g. during a toothbrushing session).

This presently fluid loading/delivery mechanism obviates the need to rely any of the following techniques: (i) 'messier' techniques which entail dipping toothbrush bristles or a sponge into a quantity of liquid (i.e. disposed at a distal portion of a rodded oral care device), where it is difficult or impossible to deliver a predictable and reproducible quality of fluid for each oral care session; (ii) other 'messier' techniques where fluid is poured into an onboard reservoir, and once again it may be difficult or impossible to deliver a predictable and reproducible quality of fluid for each oral care session; (iii) techniques that require an external device (e.g. syringe) to load the onboard reservoir; and (iv) techniques that consume expensive ampules, one ampule per oral care session.

The ability to re-supply cleaning fluid by dipping can provide flexibility and convenience—in one example, whenever additional cleaning fluid is required, the user brings a new container (e.g. sachet or jar). Unfortunately, as stated above, direct dipping of bristles or a sponge into a supply of cleaning fluid may be clinically inappropriate.

According to embodiments of the invention (i) the aforementioned inlet lumen includes an 'external' proximal tube portion (see element 411 of FIG. 4A) that protrudes from a main body of the base module; and (ii) in order to load the onboard reservoir with fluid, a proximal tip (see element 123 of FIG. 4A) of the external proximal tube portion is immersed into (e.g. see FIGS. 6A-6B, 10A, 10C) a re-supply reservoir—e.g. a jar or a sachet. This allows the user to enjoy the flexibility and convenience of dipping-based providing of cleaning fluid in a manner that is appropriate for an ICU environment.

In embodiments of the invention, the presently-disclosed fluid loading/delivery mechanism (i) enables the eased and repeatable delivery of approximately the same quantity of fluid in each oral care session; and (ii) in manner that provides flexibility and convenience of dipping-based re-supply of cleaning fluid.

Operation of a Multi-input and Multi-display Counter to Track Different Types of Oral Care Operation without Relying on Packaging or Consumption of Packaging The kit features a non-electronic multi-input and multi-display counter which is attached to and supported by the aforementioned "common hanger."

As noted above, when the kit is assembled and in use (e.g. see FIGS. 2A-2B and 7A-7B), the support element hangs from the common hanger, so that the common hanger supports the weight of both the support element and the plurality of rodded oral care devices.

The non-electronic multi-input and multi-display counter is now explained according to one particular non-limiting use case where the common-hanger-attached multi-input and multi-display counter comprises analog clock assemblies disposed next to each other—i.e. the first analog clock assembly to the left and the second analog clock assembly to the right. The first analog clock-assembly comprises a first clock dial manually rotatable around a first plurality of ticks disposed around central region where the first clock dial has a presence. The second analog clock-assembly comprises a second clock dial manually rotatable around a second plurality of ticks disposed around a central region where the second clock dial has a presence.

According to this use case: when a patient checks into the ICU, the common hanger is hung near his/her bed so that both the support element (e.g. bag or shelf or slot) and the counter (i.e. multi-input and multi-display counter) are supported by the common hanger. The support element is 'loaded' with the suction-lumened toothbrush head module, and one or more additional rodded oral care devices so the weight is supported by the common hanger. Upon check-in, each analog clock assembly of the multi-input and multi-display counter is zeroed. During the patient's stay in the ICU, the common hanger, support element (i.e. sometimes at least partially loaded), and the counter (i.e. also supported by the common hanger) remain bed-side. During the patient's stay in the ICU, the rodded oral care devices (i.e. including the suction-lumened toothbrush head module) (i.e. which are supported by the support element which in turn hangs from the common hanger) and the base module are used (i.e. by a nurse) to subject the patient to both toothbrushing sessions and a plurality of oral care sessions—each of the head module and the additional rodded oral care device(s) may be disengaged from the support element (i.e. so that the support element no longer supports the disengaged element) for use in an oral care session.

According to this use case: (i) whenever the user (e.g. nurse) performs a toothbrushing session, the first clock dial (i.e. of the first analog clock-assembly) is rotated clockwise from one tick to its clockwise immediate neighbor; and (ii) whenever the user (e.g. nurse) performs a mouth-moisturizing session, the second clock dial (i.e. of the second analog clock-assembly) is rotated clockwise from one tick to its clockwise immediate neighbor. The non-electronic multi-input multi-display counter displays two count states indicated by: (i) the current tick/point-position of the first analog clock assembly and (ii) the current tick/point-position of the second analog clock assembly.

In this manner, there is no need to rely on packaging to count oral care operations, and it is clear to any nurse in the ICU who visits the patient's bed how many toothbrushing sessions have been performed on the patient, and how many mouth-moisturizing sessions have been performed on the patient. This will help the nurse decide if the next treatment to the intubated patient will be a toothbrush treatment or a mouth moisturizing treatment.

Since the support element and the multi-input and multi-display counter (i.e. both of which are supported by and hang by the common hanger) remain by the patient's bedside during an entirety of his/her stay in the ICU, this information (i.e. about the previous number of treatments of the first and second types) is readily available to any nurse in the ICU.

Since this information about the absolute and relative numbers of previous treatment of each type is readily available, there is no need to individually provide different types of oral care packs within compartments of a multi-compartment packaging, such as that disclosed in U.S. Pat. No. 7,866,477.

Thus, in some embodiments, the presently-disclosed teachings allow for the hospital to do away completely with per-patient oral-care kits of the type disclosed in U.S. Pat. No. 7,866,477.

When a nurse approaches a given patient, s/he can check the non-electronic multi-display multi-input counter (e.g. hanging from the common hanger that is disposed near the patient's bed) to read, from this non-electronic multi-display multi-input counter, the number of previous treatments of each type applied to the patient. As such, the nurse can instantly ascertain the next type of oral-care treatment required in the oral care cleaning cycle, take the appropriate oral care operation-performing elements(s) (e.g. in a treatment pack) from the support element (e.g. any substrate-board-mounted storage compartment (e.g. any of 936A-936C), and subject the patient to this oral-care cleaning procedure using the oral care element(s). If appropriate (e.g. if the oral-care cleaning procedure involves brushing the patient's teeth), this oral care procedure may be performed using the base module 100 as a toothbrush handle.

BRIEF DESCRIPTION OF THE DRAWINGS

FIG. 1A illustrates a prior art oral care kit.

FIGS. 1B-1D illustrate prior art rodded oral care devices.

FIGS. 5A-5B respectively illustrate the head and base modules when not the assembled configuration of FIG. 4A.

FIGS. 6A-6D illustrate loading of fluid into the onboard reservoir and subsequent discharge from the fluid therefrom.

FIG. 10A illustrates an example where a proximal end of a proximal tube portion of an inlet lumen is immersed in (e.g. dipped in) a container of cleaning fluid before this fluid subsequently loaded form the container to an onboard reservoir of the base module.

FIGS. 11A-11B illustrate the outline of the proximal tube portion respectively for the examples of FIGS. 10C-10D.

DETAILED DESCRIPTION OF EMBODIMENTS

Figure 4A:
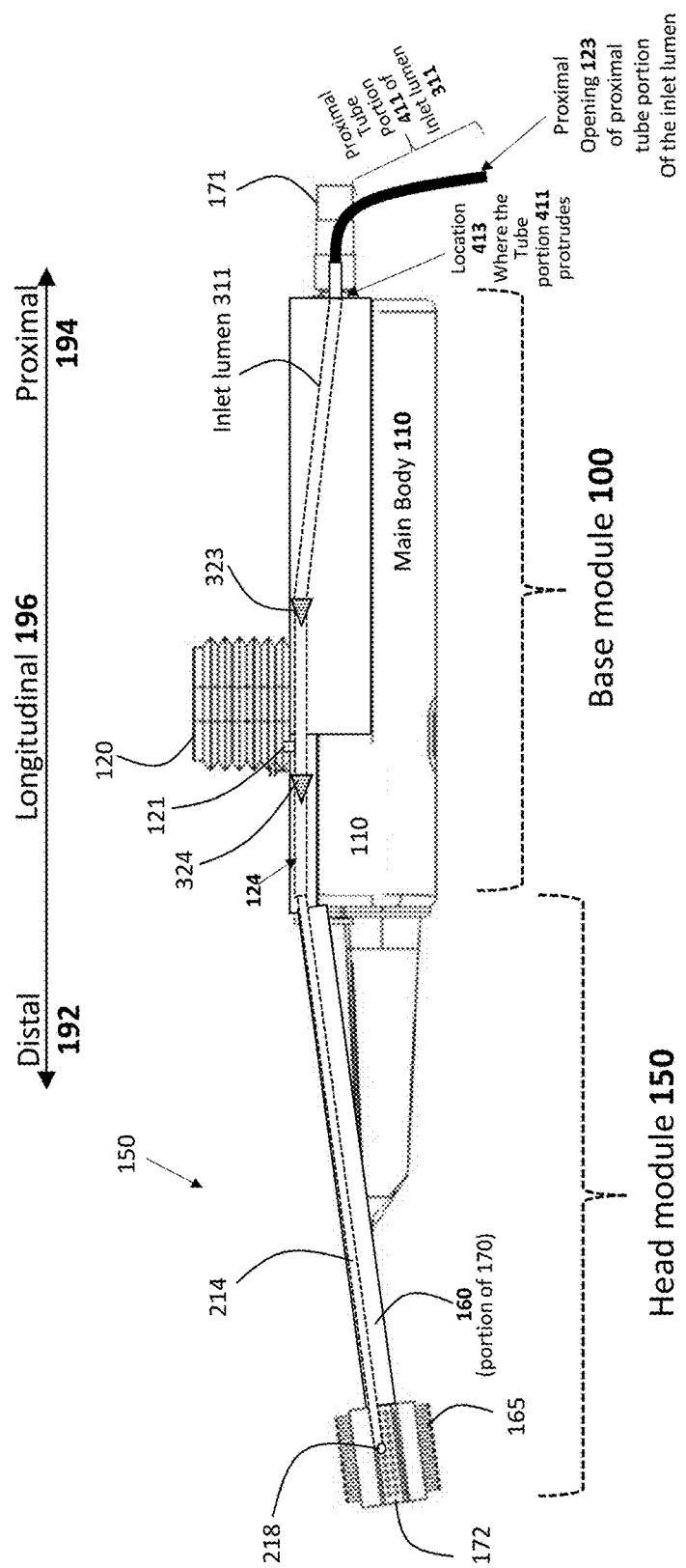
FIGS. 4A-4C illustrate the base and head module in an assembled configuration where FIG. 4A emphasizes elements related to fluid delivery and FIGS. 4B-4C emphases elements related to suction.

Embodiments of the invention relate to an oral care kit comprising:
- a. a base module—for providing a fluid loading/unloading mechanism (e.g. see FIGS. 6A-6D)).
  One example of a base module 100 is shown in FIGS. 4A and 6B and includes: (i) an onboard compressible fluid reservoir 120 (e.g. see FIG. 4A); (ii) an onboard inlet lumen 311 (e.g. see FIG. 4A); (iii) a proximal tube portion 411 of onboard inlet lumen 311 (e.g. see FIG. 4A); (iv) main body 110 of the base module 100 (e.g. see FIG. 4A); (v) a proximal opening 123 of the proximal tube portion 411 (e.g. see FIG. 4A); (vi) a first one-way valve 323, a base-module-onboard fluid-delivery lumen section 124 (e.g. see FIG. 4A); (vii) a second one-way valve 324 (e.g. see FIG. 4A); (viii) a base-module onboard suction lumen section 370 (e.g. see FIG. 5B—for example, having proximal suction connector 171);
- b. a plurality of rodded oral care devices—e.g. examples of rodded oral care devices are shown in FIGS. 1B-1D, 5A and 9; one or more of the rodded oral care devices may have features of head module 150 of FIG. 5A and/or of elements 1204A-1204F of FIG. 7A and/or of FIG. 9;
- c. a hanger—e.g. examples include element 998 of FIG. 2A or 2B;
- d. a support element that hangs from the hanger 998—examples of the support element may include any compartment 936A-936C of FIG. 2A or any bag 97A or 97B of FIG. 2B;
- e. a non-electronic multi-input multi-display counter 149—e.g. see element 149 of FIG. 2A. The non-electronic multi-input multi-display counter 149 may be used to track multiple types of oral care operations—for example, operations performed by one or more of the oral care devices (e.g. 1240A-1204F).

Figure 4B:
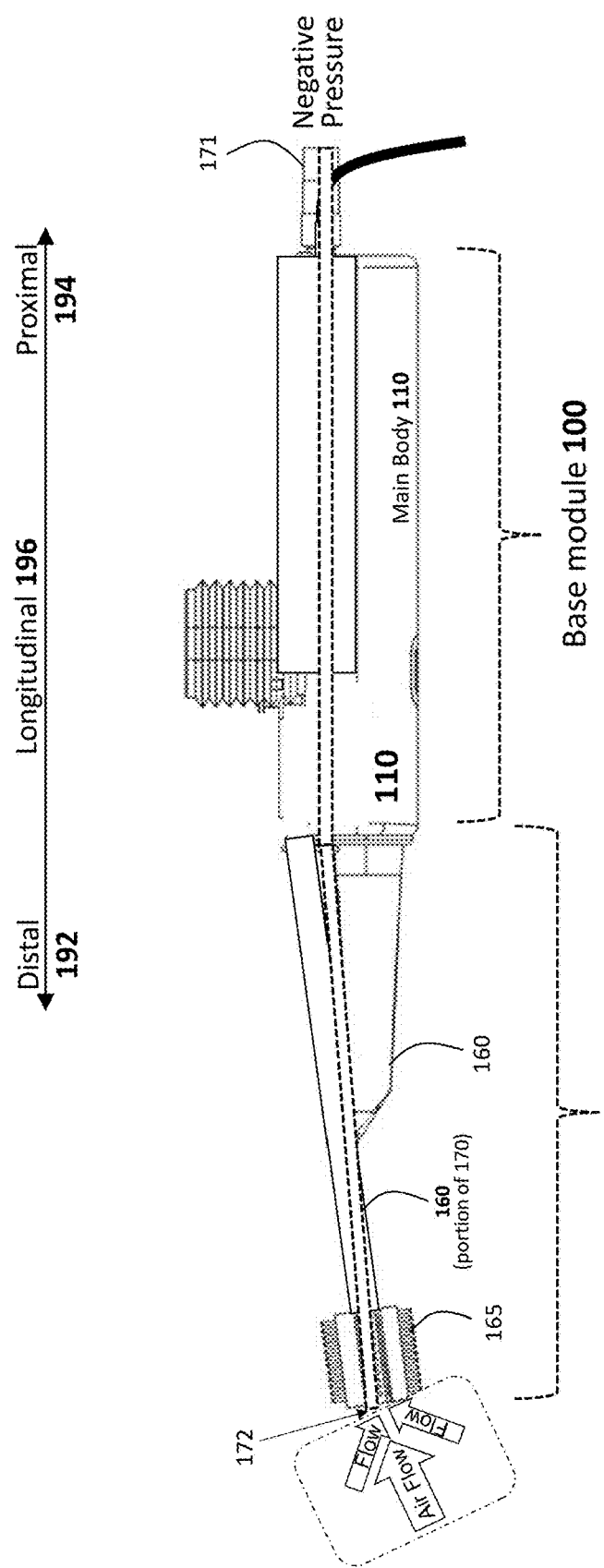
Figure 4C:
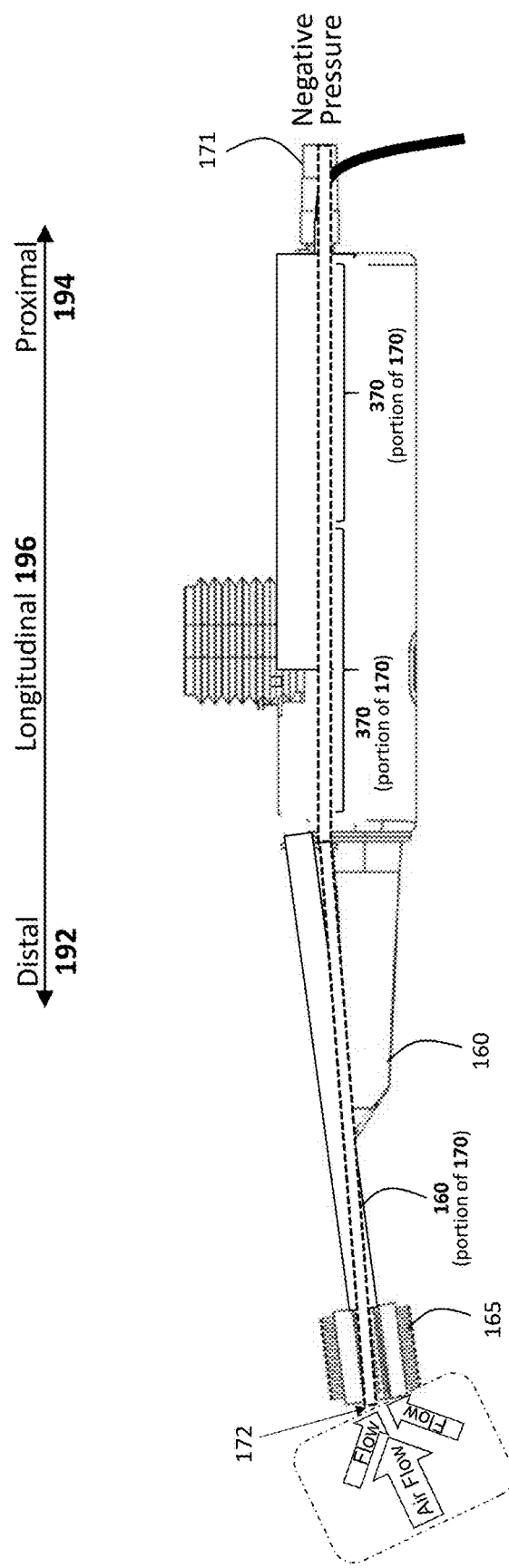
Figure 10B:
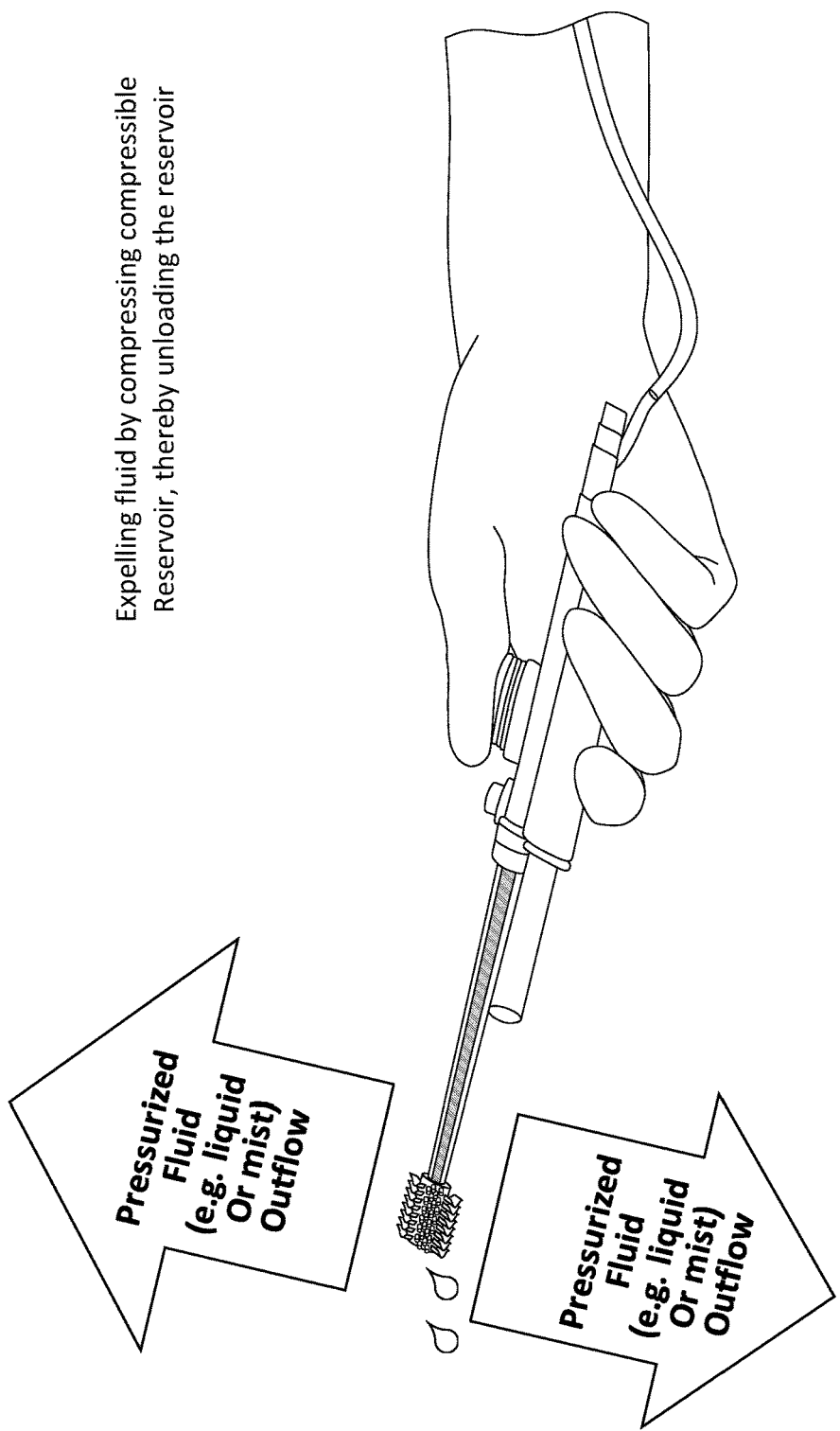
FIG. 10B illustrates a device as fluid is expelled from the onboard reservoir of the base module.

Assembly-related features—FIGS. 4A-4C illustrate the base and head module in an assembled configuration while FIGS. 5A-5B respectively illustrate the head and base modules when not the assembled configuration of FIG. 4A. The suction-lumened toothbrush 150 is detachably attachable to the base module 100 to form an oral care device (i.e. shown in FIGS. 4A-4C) so that upon attachment:
- (i) as shown in FIGS. 4B-4C the respective suction lumen sections 160, 370 form a continuous suction lumen 170 along a length of oral care device (i.e. to transmit negative pressure from a proximal end of the suction lumen 170—for example, at connector 171—to the distal end of the suction lumen—for example, at distal suction orifice 172; and
- (ii) as shown in FIG. 4A, the respective fluid-delivery sections 214, 124 form a continuous fluid-delivery lumen (NOT LABELLED WITH A NUMBER) that provides fluid communication between an interior of the fluid reservoir 120 and the fluid-delivery orifice 218 (e.g. for delivery of fluid as shown in FIGS. 6D and 10B).

The figures illustrate an oral care kit comprising:
- a. a base module 100 comprising:
  - i. an onboard compressible fluid reservoir 120 having an equilibrium size so that, when released from a compressed configuration, a restoration force urges size-increase of the reservoir back to the equilibrium size;
  - ii. an onboard inlet lumen 311 comprising a proximal tube portion 411 that:
    - A. protrudes from a main body 110 of the base module; and
    - B. has a proximal opening 123,
    the inlet lumen 311 providing fluid communication between the proximal opening 123 of the proximal tube portion and the compressible fluid reservoir for loading thereof;
  - iii. a first one-way valve 323 disposed between the proximal opening 123 of the proximal tube portion of the inlet lumen 311 and the compressible fluid reservoir 120 so as to permit fluid inflow past the first one-way valve 323 towards the fluid reservoir and to block fluid backflow from the reservoir in the opposite direction;
  - iv. a base-module-onboard fluid-delivery lumen section 124;
  - v. a second one-way valve 324 disposed in the onboard fluid-delivery lumen section 124 to permit fluid outflow of fluid flowing from the reservoir 120 past the second one-way valve 324 and to block fluid backflow towards the reservoir 120 in the opposite direction;
  - vi. a base-module onboard suction lumen section 370 that does not lead into the fluid compressible reservoir 120;
- b. a plurality of rodded oral care devices, at least one of which is a suction-lumened-toothbrush including an head-module onboard suction lumen section 160, an onboard fluid-delivery-lumen section 214 having a fluid-delivery-orifice 218 at a distal end of the head-module-onboard fluid-delivery-lumen section 214, and a plurality 165 of toothbrush bristles;
- c. a hanger 998;
- d. a support element 936A-936B that hangs from the hanger 998, the support element for supporting each rodded oral care device of the plurality of devices;
- e. a non-electronic multi-input multi-display counter 149 attached to and supported by the hanger 998 the multi-input/multi-display counter independently displaying first and second count-states, the multi-input multi-display counter including first and second independently-operable user inputs respectively associated with the first and second count states such that:
  - (I) in response to user engagement of the first user input, the first count state is incremented or decremented; and
  - (II) in response to user engagement of the second user input, the second count state is incremented or decremented; and wherein:
i. the suction-lumened toothbrush is detachably attachable to the base module to form an oral care device so that upon attachment:
   A. the respective suction lumen sections 160, 370 form a continuous suction lumen along a length of oral care device; and
   B. the respective fluid-delivery sections 214, 124 form a continuous fluid-delivery lumen that provides fluid communication between an interior of the fluid reservoir and the fluid-delivery orifice;
ii. after attachment, expansion of the fluid reservoir from an at-least partially compressed configuration loads the fluid reservoir so that a negative pressure created within the expanding reservoir suctions fluid past the first one-way valve into the fluid reservoir while a presence of the second one-way valve blocks back-flow through the base-module-onboard fluid-delivery lumen section 124 and into the fluid reservoir 120;
iii. after attachment and after loading, compression of the fluid reservoir 120 unloads the fluid reservoir 120 to force the unloaded fluid to exit the fluid-delivery orifice 218 so that outflow from the fluid reservoir flows through the continuous fluid-delivery lumen formed by the attachment and past the second one-way valve 324 while a presence of the first one-way valve 323 prevents flow of fluid from passing back towards proximal opening 123 of the inlet lumen 311.

In relation to the figures the following numbers indicate:

Modules

100—Base module
150—Head Module (e.g. suction-lumened toothbrush device)

Elements of Multi-input/Multi-display Counter 149 (e.g. Comprising First 147A and Second 147B Single-input Counters)

146—first user-input of multi-input/multi-display counter 149 (e.g. a first manually-rotatable pointer of the first 147A single-input counter)
144—first counter-state visualization element (e.g. first plurality of ticks disposed around a rotation-center of the manually-rotatable pointer 146) for visualizing a first count-state (i.e. if there are N ticks there are N count-states defined by the combination of 146 and
144—the tick to which the rotatable-pointer 146 points to defines the first 'count-state')
145—second user-input of multi-input/multi-display counter 149 (e.g. a second manually-rotatable pointer of the second 147B single-input counter)
143—second counter-state visualization element (e.g. second plurality of ticks disposed around a rotation-center of the manually-rotatable pointer 145) for visualizing a second count-state (i.e. if there are N ticks there are N count-states defined by the combination of
145 and 143—the tick to which the rotatable-pointer 145 points to defines the second 'count-state')

Fluid-delivery Related (e.g. See FIGS. 4A; 6A-6D)

214—fluid delivery lumen section of head module 150
218—distal fluid delivery orifice of fluid-delivery lumen 214
120—base-module-residing liquids reservoir/container (e.g. reservoir)
121—inlet/outlet hole of liquid reservoir/container (i.e. distally-flowing fluids from inlet lumen enter reservoir 120 via hole 121 in FIG. 6B; distally-flowing fluids leave reservoir
120 via hole 121 in FIG. 6D)
311—refill/inlet lumen for refilling liquids reservoir/container 120
411—proximal tube portion 411 of refill/inlet lumen 311
123—proximal opening to/end of (and thus the proximal opening of the onboard inlet lumen 311)—functioning as an input port
413—protrusion location where the proximal tube portion 411 of refill/inlet lumen 311 protrudes from main body 110 of the base module 100
218—distal fluid lumen orifice of head module 150
214—portion of the fluid delivery lumen residing in the head (e.g. suctioned-lumen)
323—proximal uni-directional/one-way valve between proximal fluid inlet/opening 123 to tube or lumen 311 and pump chamber/reservoir 120 (i.e. the 'first' one-way valve)
124-base-module-onboard-fluid-delivery lumen section
324—distal uni-directional/one-way valve between pump chamber/reservoir 124 and distal orifice 218 (e.g. on base-module-onboard-fluid-delivery section 124) (i.e. the 'second' one-way valve)

Suction-related (e.g. See FIGS. 4B-4C; 5A-5B)

370—base-module-residing suction lumen that is not in fluid communication with and separate from reservoir 120 and fluid-delivery lumen 214 or refill lumen/tube 311
160—suction lumen portion of head section 150 (e.g. suction-lumened toothbrush) (see FIG. 4B or 4C or 5A)
171—proximal suction connector (e.g. see FIGS. 4A-4C or 5B)
170—a suction lumen formed, when the head 150 and base 100 are coupled, by the combination of 370 and 160 so that negative pressure applied to connector 171 is transmitted to distal suction orifice 172
172—distal suction orifice of suction lumen 170 (e.g. see any of FIGS. 4A-4C or 5A)

Toothbrush-related Element (e.g. Optional Power Brush)

Figure 2A:
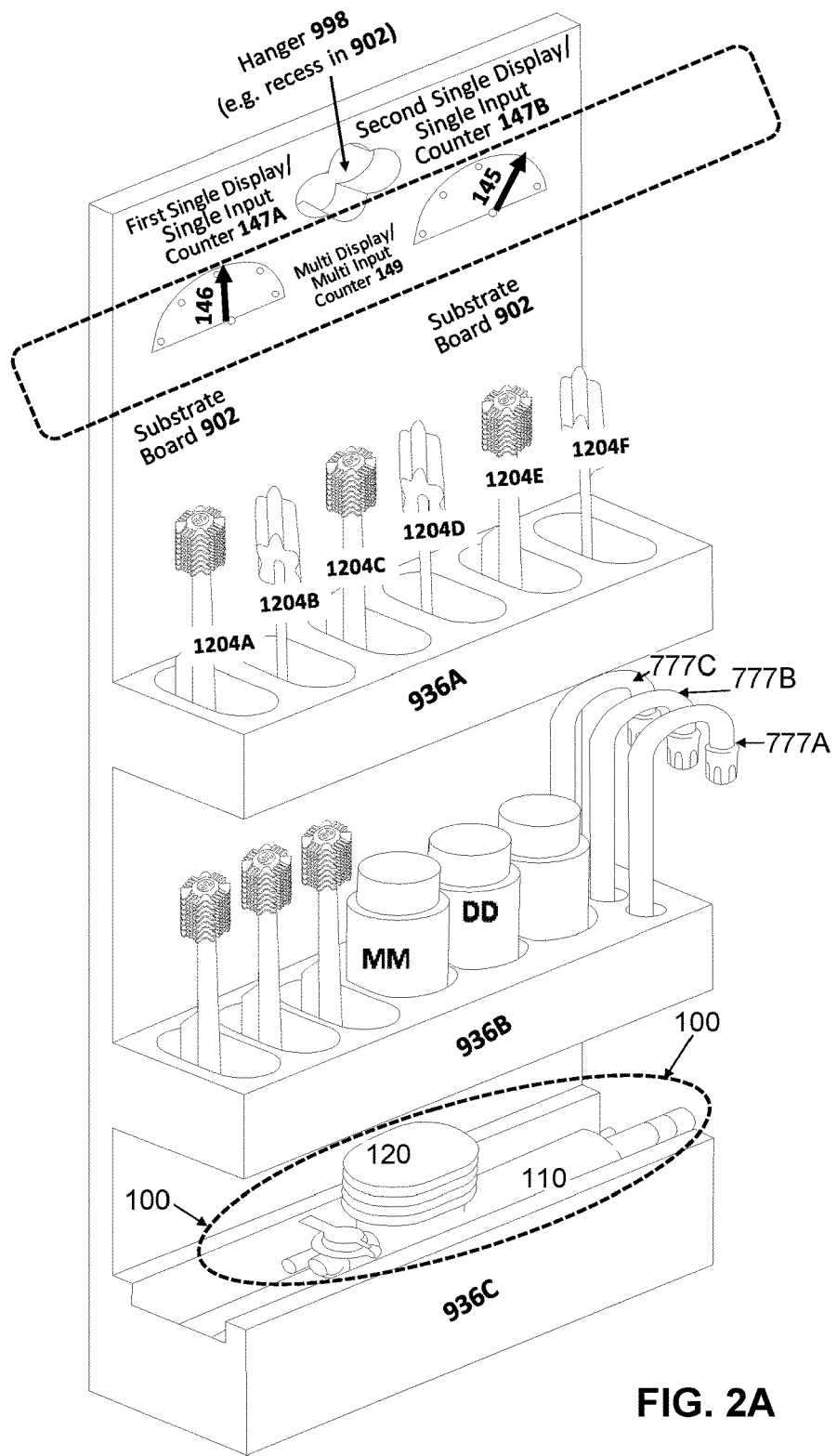
FIG. 2A-2B illustrate components of an oral care kit assembled in a hanging configuration according to first and second examples.

165—toothbrush bristle brush disposed on the head module 150—a toothbrush bristle brush is a brush of toothbrush bristles. The toothbrush bristles of the brush are disposed on (and retained on) on a surface (e.g. of element 161) head module 150—this surface is referred to as a 'toothbrush-retaining' surface.
NOT SHOWN—motor (e.g. base-module-residing)
179—sheath of head module 150
177—proximal-facing cavity of head module 150 (e.g. interior of sheath 179 into which distal portion 158 tip thereof)
Axis/direction
196—Longitudinal axis
194—proximal direction
192—distal direction FIG. 2A illustrates components of an oral care kit assembled in a hanging configuration. Oral care operation-performing elements (e.g. rodded oral care devices 1204A-1204E, suction elements 777A-777C, containers labelled as "MM" and "DD", and base module 100, all discussed below) are disposed within storage compartments 936A-936C and physically supported by these compartments. For example, the hanging-configuration assembled kit hangs near a particular patient's bed (e.g. and remains there for some time), oral care operation-performing elements are removed from their storage compartments and used to subject the particular patient (e.g. by a nurse or other practitioner) to multiple types of oral care operations.

Figure 2B:
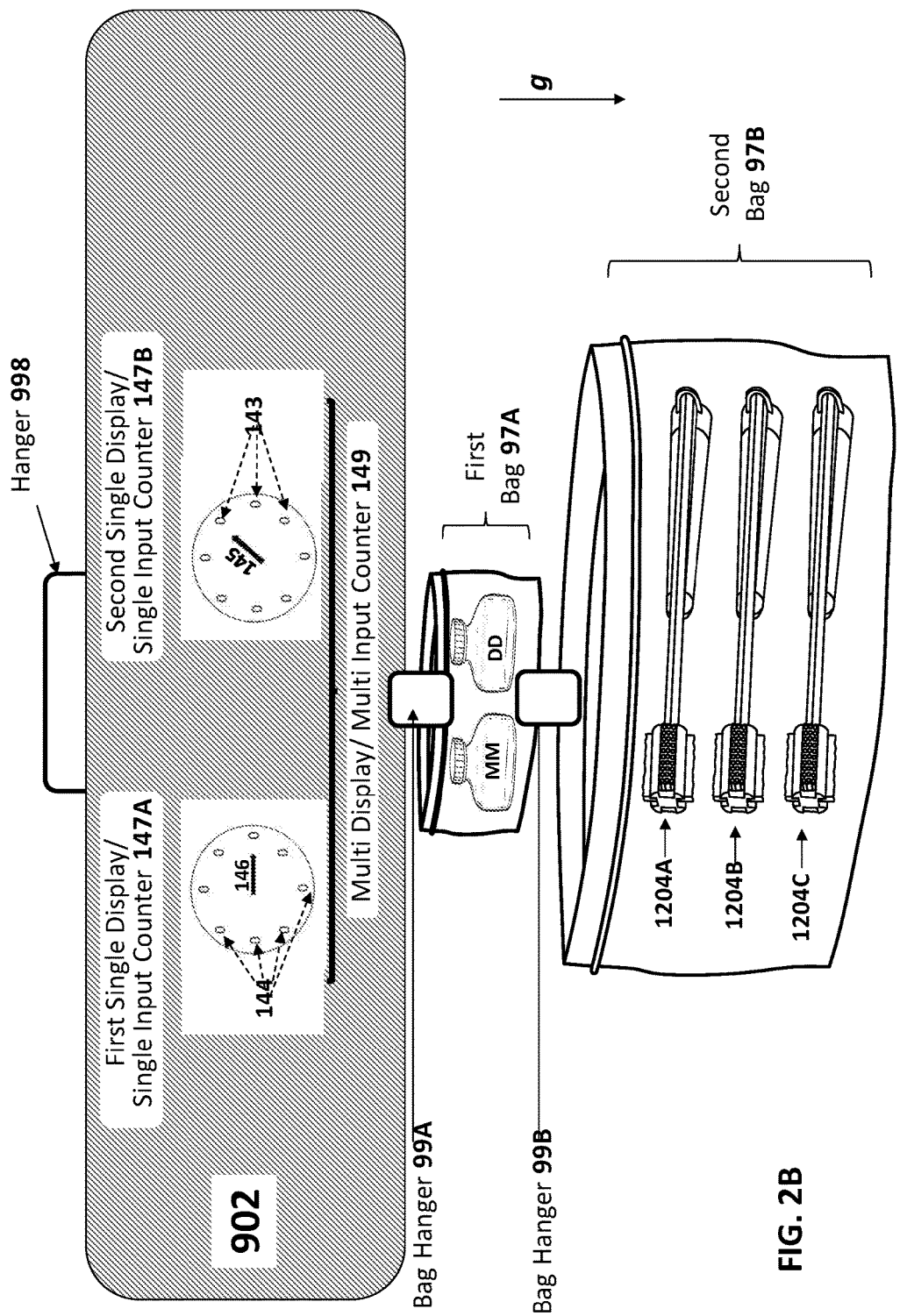

FIG. 2B illustrates another example of an oral care kit assembled in the hanging configuration including bag hangers 99A-99B and bags 97A-97B. Rodded oral care devices 1204A-1204 are disposed within bag 97B. In the example of FIG. 2B, a bag is an example of a support element.

Some oral care operation-performing elements are consumable (e.g. rodded oral care devices such as toothbrush head 150—one example of a rodded oral care device 1204A-1204E), and are typically used just once and not returned to one of the storage compartments. Other oral care operation-performing elements may be re-usable—e.g. after base 100 is removed from storage compartment 936C and used it may in a toothbrushing session (e.g. employing the fluid-loading delivery mechanism discussed below with reference to FIGS. 6A-6D). Subsequently, re-usable base 100 may be returned to storage compartment 936C for later use in a later and distinct oral-care treatment or session.

Multiple types of oral care operations (e.g. performed by one or more of the oral care operation-performing elements of the illustrated kit) are manually tracked by a user (e.g. a nurse) using non-electronic multi-input/multi-display counter 149. Both counter 149 and storage compartments 936A-936C are mounted to substrate board 902.

In embodiments of the invention, the kit of FIG. 2 (e.g. in particular counter 149) enables separate tracking of both the following types of oral care operations: (i) mouth-moisturizing operations or sessions and (ii) toothbrushing operations or sessions—i.e. in a manner which does not rely on packaging, or consumption of packaging (e.g. packing of oral care operation-performing elements). The skilled artisan is directed, for example, to FIGS. 3A-3B, 7A-7F and 8 and the section entitled 'tracking oral care sessions/operations'.

In the example set-forth above where substrate board 902 hangs near a patient's bed (e.g. like a chart) during his/her stay in the ICU, hospital personnel passing near the patient's bed can view on counter 149 the number of oral care operations/sessions of each type to which the patient was previously subjected. This may replace the common practice where the number of previously-performed operations is deduced based on an quantity (or count) of consumed or unconsumed packaging (i.e. packing of oral care operation-performing elements).

As shown in FIG. 2A, in addition to counter 149, substrate board 902 also supports various oral care operation-performing elements—these supported oral care operation-performing elements may be used to perform the oral care operations which are tracked by manual operation of non-electronic counter 149.

Performing oral-care operations using oral care operation-performing elements—For performing oral-care operations, the kit of FIG. 2 includes (i) a base module 100 of a multi-module toothbrush device; and (ii) a plurality of rodded oral care devices 1204A-1204E, at least one of which is head module 150 of the multi-module toothbrush device. The base module 100 and the head module 150 are shown in FIG. 4A (assembled configuration to form the toothbrush device) and FIGS. 5A-5B (unassembled configuration). As will be discussed below with reference to FIGS. 6A-6D, the multi-module toothbrush provides a novel fluid loading/delivery mechanism for loading fluid into reservoir 120 and for delivery of fluid (for example, disinfectant fluid from 'DD" 1252) from onboard reservoir 120 of base module 150.

The skilled artisan is directed to the discussion of the fluid loading/delivery mechanism (e.g. for the purpose of introducing fluid during toothbrushing sessions) below, with reference to FIGS. 6A-6D.

Tracking oral care operations using the multi-input/multi-display counter 149 that is mounted to Substrate board 902—one salient feature of the kit of FIG. 2A is that hangable substrate board 902 (e.g. including hanging element 998) has two roles: (i) substrate board 902 serves as a mount of multi-input/multi-display counter 149 and (ii) together with a mounted storage compartment array of compartments 936A-936C, substrate board 902 serves to support the elements used to perform the oral care operations.

The current section relates to both features of the non-electronic, multi-input and multi-display counter 149 and its use in tracking multiple types of oral care operations (e.g. performed by or using material of one or more oral care operation-performing elements illustrated in FIG. 2A. For example, one type of oral care operation is a toothbrushing session and the other is a soft-tissue-lubrication session.

The non-electronic multi-input and multi-display counter (shown in FIGS. 2A and 3A) is now explained according to one particular non-limiting use case where the substrate-board-mounted multi-input and multi-display counter 149 comprises analog clock assemblies 147A, 147B mounted next to each other on the substrate board—i.e. the first analog clock assembly 147A to the left and the second analog clock assembly 147B to the right. The first analog clock-assembly 147A comprises a first clock dial 146 manually rotatable around a first plurality 144 of ticks. The second analog clock-assembly 147B comprises a second clock dial 145 manually rotatable around a second plurality of ticks 143.

Figure 3C:
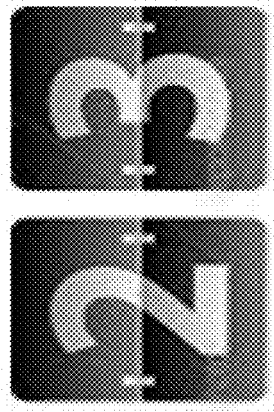
FIGS. 3C-3D illustrate examples of single-input counters.
Figure 3D:
Figure 3A:
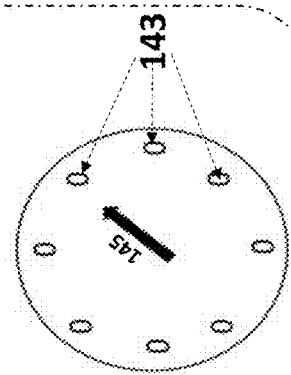
FIG. 3A illustrates one example of a non-electronic multi-input and multi-display counter.
Figure 3B:
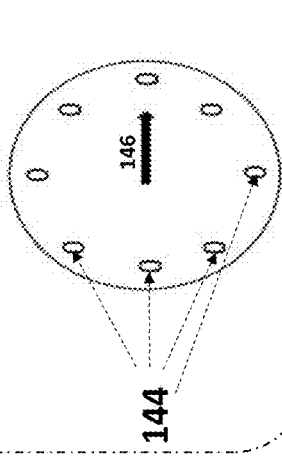
FIG. 3B illustrates manual incrementing of a count-state.

FIG. 3B illustrates manual incrementing of a count-state by rotating dial 146 from one of the ticks 144 to another one (e.g. its neighbor).

Figure 9:
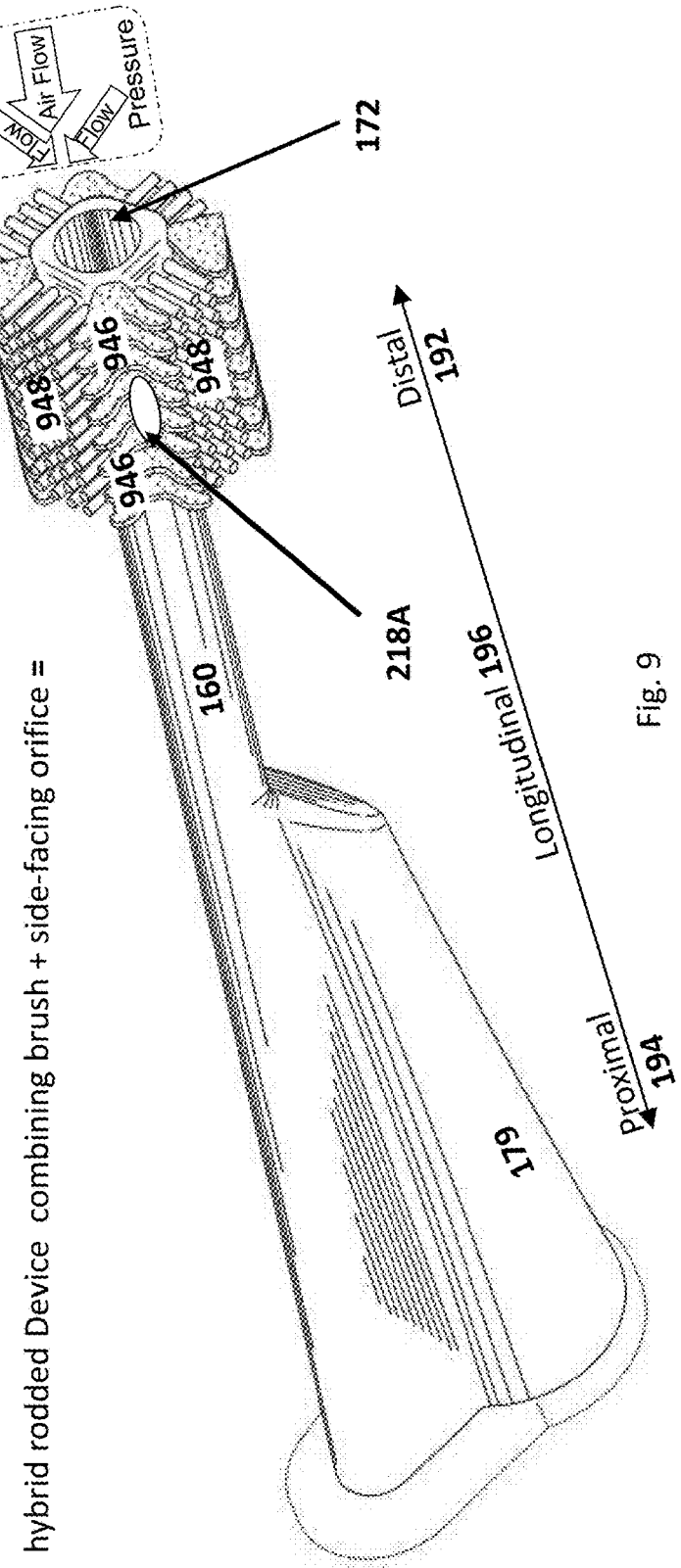
FIG. 9 illustrates an example rodded oral care device.

According to one non-limiting use case: when a patient checks into the ICU, the substrate board 902 is hung near his/her bed (e.g. via hanger 998), and the storage compartment(s) 936A-936C are loaded with the base module 120 (i.e. including main body 110), and one or more suction-lumened toothbrush head modules (e.g. one of 1204A-1204F—this corresponds to 150 of FIG. 5A) (in another example, the suction-lumened toothbrush head module is that of FIG. 1B), and one or more additional rodded oral care devices (i.e. which may or may not be suction-lumened toothbrush head modules—e.g. in non-limiting examples, any of FIGS. 1B-1D or head module of FIG. 5A of the device of FIG. 9 may be used). Once the suction-lumened toothbrush head module(s) is(are) in storage compartment(s) 936A-936C and shown in FIGS. 2A-2B, they are supported by the substrate board 902, which supports the storage compartment(s).

Figure 7A:
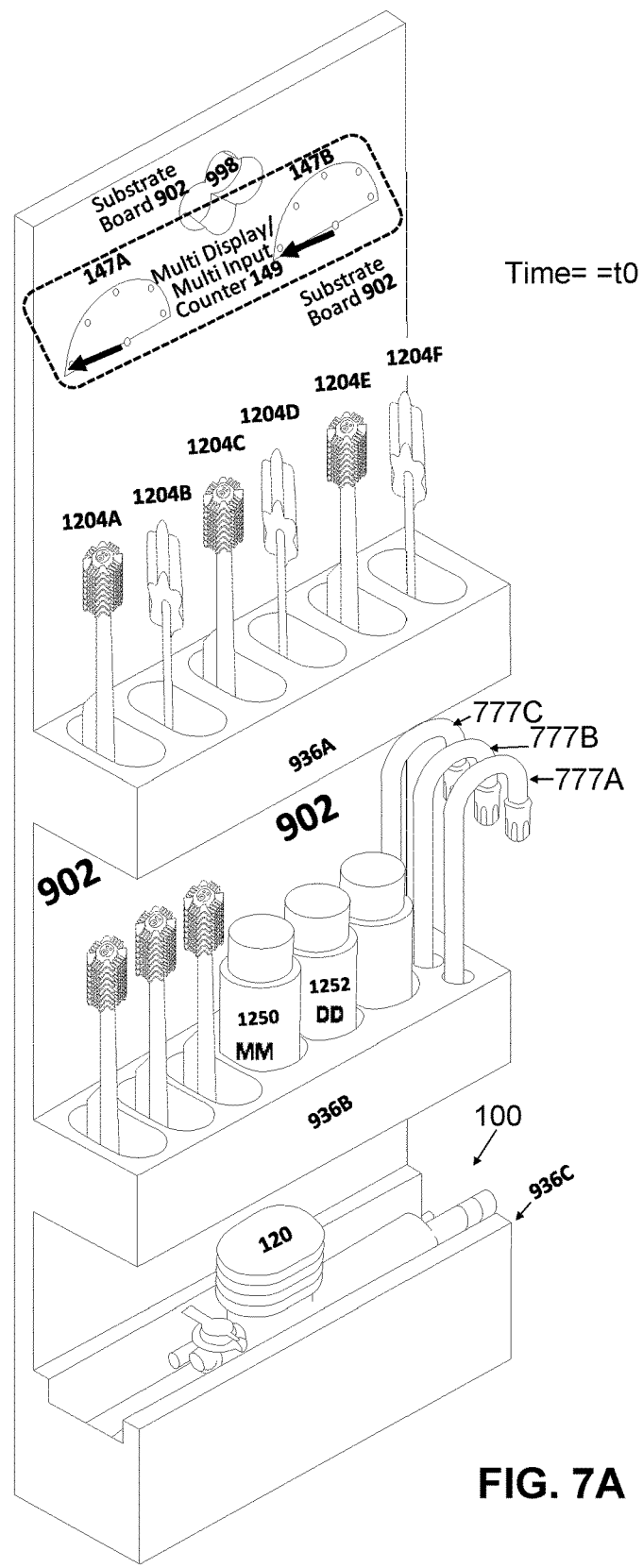
FIGS. 7A-7F respectively show a state of one example kit (in hanging configuration) respectively at times T=t0-t5.

Upon patient check-in, each analog clock assembly 147A, 147B is zeroed e.g. to a state shown in FIG. 7A. During the patient's stay in the ICU, the substrate board 902, the substrate-board-mounted counter 149, and the substrate-board-mounted storage container(s) (i.e. sometimes at least partially loaded) remain bed-side. In this non-limiting use case, during the patient's stay in the ICU, the rodded oral care devices (i.e. including the suction-lumened toothbrush head module 150) and the base module 100 (i.e. which are stored in the substrate-board-mounted storage compartment(s)) are used (i.e. by a nurse) to subject the patient to both toothbrushing sessions and a plurality of oral care sessions—each of the base module 100, the head module 150 and the additional rodded oral care devices 1204B-1204F may be removed from the substrate-board-mounted storage compartment(s) 936A-936C for use in an oral care session.

According to this non-limiting use case: (i) whenever the user (e.g. nurse) performs a toothbrushing session, the first clock dial 146 (i.e. of the first analog clock-assembly 147A) is manually rotated clockwise (e.g. by the user such as a nurse) from one tick (e.g. of the ticks 144) to its clockwise immediate neighbor (see, for example, FIG. 3B); and (ii) whenever the user (e.g. nurse) performs a mouth-moisturizing session, the second clock dial 145 (i.e. of the second analog clock-assembly 147B) is rotated clockwise (e.g. by the user such as a nurse) from one tick (e.g. of the ticks 146) to its clockwise immediate neighbor. The non-electronic multi-input multi-display counter 149 displays two count states indicated by: (i) the current tick/point-position of the first analog clock assembly 147A and (ii) the current tick/point-position of the second analog clock assembly 147B.

In this manner, there is no need to rely on packaging (e.g. packaging of any of the oral care operation-performing elements) to count oral care operations, and it is clear to any nurse in the ICU who visits the patient's bed how many toothbrushing sessions (e.g. by viewing a position of pointer 146 relative to ticks 144) have been performed on the patient, and how many soft-tissue-moisturizing sessions (e.g. by viewing a position of pointer 145 relative to ticks 143) have been performed on the patient. This will help the nurse decide if the next treatment to the intubated patient will be a toothbrush treatment or a mouth moisturizing treatment.

Since (i.e. according to this example) the hanging substrate board 902 (e.g. having both the multi-input multi-display counter 149 as well as containers or compartments 936A-936C where the base 120 and rodded oral care devices 1204A-1204F are stored) remains by the patient's bedside during an entirety of his/her stay in the ICU, this information (i.e. about the previous number of treatments of the first and second types—information to be read from counter 149) is readily available to any nurse in the ICU.

Since (i.e. according to this example) this information about the absolute and relative numbers of previous treatment of each type is readily available (e.g. to be read from counter 149), there is no need to individually provide different types of oral care packs within compartments of a multi-compartment packaging, such as that disclosed in U.S. Pat. No. 7,866,477.

Thus, in some embodiments, the presently-disclosed teachings allow for the hospital to do away completely with per-patient oral-care kits of the type disclosed in U.S. Pat. No. 7,866,477.

When a nurse approaches a given patient, s/he can check the non-electronic multi-display multi-input counter mounted 149 on the substrate board 902 (e.g. disposed near the patient's bed) to read, from this non-electronic multi-display multi-input counter 149, the number of previous treatments of each type applied to the patient.

As such, the nurse can instantly ascertain the next type of oral-care treatment required in the oral care cleaning cycle, take the appropriate oral care operation-performing element(s) (e.g. in a treatment pack) from the appropriate storage compartment (e.g. one of 936A-936C), and subject the patient to this oral-care cleaning procedure using the oral care element(s) obtained from the appropriate bag. If appropriate (e.g. if the oral-care cleaning procedure involves brushing the patient's teeth), this oral care procedure may be performed using a main body of the base module 100 as a toothbrush handle.

As shown in FIG. 2, compartments 936A-936C are slots—in non-limiting examples, they may be shelves or bags.

In some embodiments, a thickness of substrate board 902 is at most 2 cm or at most 1 cm.

Any hanger described or disclosed herein is 'optional' in any embodiment.

Embodiments of the present invention relate to a rodded oral care device which may be (i) a toothbrush device having an onboard toothbrush (e.g. plurality or field of bristles) (e.g. suction-lumened-toothbrush) or a (ii) fluid applicator device (e.g. having a fluid-delivery lumen through which fluid is actively forced into the mouth or a more 'passive' fluid applicator device such as a sponged rod or a swab device).

A Discussion of Counter 149 of FIGS. 2A, and 3A-3D

In the non-limiting example of the figures, multi-input/multi-display counter 149 is mechanical and comprises first and second user-input. For example, the inputs are first 146 and second 145 manually-rotatable pointers. In this example, the multi-input/multi-display counter 149 comprises first 144 and second 143 visualization elements—for example, first and second pluralities of ticks. The first plurality of ticks 144 is disposed around a center of rotation of the first 146 rotatable pointer. The second plurality of ticks 143 is disposed around a center of rotation of the second 145 rotatable pointer.

The multi-input/multi-display counter 149 independently displays first and second count-states. In the particular example of the drawings, the first count-state is the relative position of first rotatable pointer 146 relative to the first plurality of ticks 144, and the second count-state is the relative position of second rotatable pointer 145 relative to the second plurality of ticks 143.

Furthermore, multi-input/multi-display counter 149 includes first and second independently-operable user inputs (in this non-limiting example, the first 146 and second 144 rotatable pointer which rotate around different centers) that are respectively associated with the first and second count-states (in this example, the relative positions of the pointers with respect to the ticks respectively define).

Multi-input/multi-display counter 149 further provides the following feature—in response to user engagement (e.g. manual rotation of rotatable pointer 146 from one marker/tick to its neighbor)) of the first user input (i.e. the rotatable pointer 146), the first count state (e.g. the angular position of pointer 146 relative to its set of ticks 144) is incremented or decremented. For example, rotation in one direction to transition the pointer 146 orientation between neighboring ticks (e.g. from a first tick (i.e. of the set of ticks 144) to a neighboring tick that is to the right of the first tick) will serve to increment the count, and rotation in the opposite direction (i.e. counterclockwise) from a the first tick to a neighboring tick that is to the will serve to decrement the count.

Multi-input/multi-display counter 149 further provides the following feature—in response to user engagement (e.g. rotation of pointer 145)) of the second user input (i.e. the rotatable pointer 145), the second count state (e.g. the position of pointer 145 relative to its set of ticks 143) is incremented or decremented. For example, rotation in one direction to transition the orientation of rotatable pointer 145 between neighboring ticks (e.g. from one tick of the second set of ticks 143 to a neighboring tick of the second set of ticks 143) will serve to increment the count, and rotation in the opposite direction will serve to decrement the count.

The term 'multi-input' means the counter 149 has two inputs—in the example of FIG. 3A pointer 145 is the first input and pointer 144 is the second input.

The term 'multi-display' means the counter is able to independently display (i) a first count-state (i.e. defined by the orientation of pointer 146 relative to the ticks 144—i.e. which specific and discrete tick (of the ticks 145) pointer 146 is pointing to) and (ii) and a second count-state (i.e. defined by the orientation of pointer 145 relative to the ticks 143—i.e. which specific and discrete tick (of the ticks 143) pointer 145 is pointing to.

One example of 'incrementing' a count state is shown in FIG. 3B—in this example, the 'user input' is the single rotatable pointer which is engaged by manual rotation and responds to the manual rotation by moving from one tick to its neighbor, thereby incrementing the displayed count-state.

In some embodiments, motion of an oral care device (or motion of a container of the brush—e.g. detaching the container from an object to which is attached) does not increment or decrement either count states—i.e. it is possible to increment or decrement the first and/or second count states (ie. by 'user input') without moving any oral care device and/or any container thereof.

A Discussion of FIGS. 7A-7F and 8

A non-limiting example is now discussed with reference to FIGS. 7A-7F and 8.

FIGS. 7A-7F respectively show a state of the kit at times T=t0-t5.

At time T=t0 (shown in FIG. 7A) the system is preloaded with devices 1204A-1204F, 100, and 777A-777C. In the non-limiting example of FIG. 7A, (i) rodded oral care devices 1204A, 1204C, 1204E are suction-lumened-toothbrush devices corresponding to head module 150 for use with base module 100; and (ii) rodded oral care devices 1204B, 1204D, 1204F are sponged rod devices (e.g. corresponding to FIG. 1D) lacking toothbrush bristles. In one non-limiting examples, one or more of the suction-lumened toothbrush devices 1204A, 1204C, 1204E are as in FIG. 9.

In different embodiments, (i) the suction-lumened toothbrush devices 1204A, 1204C, 1204E are used in toothbrushing operations/sessions (e.g. using fluid DD in container 1252) that are manually tracked using counter 147A; and (ii) the sponged rod devices 1204B, 1204D, 1204F are used in soft tissue moisturizing operations/sessions (e.g. using fluid MM in container 1250) that are manually tracked using counter 147B.

At a later time that is both after time T=t0 and before time T=t1, one of the suctioned-lumened toothbrush devices 1204A is removed from compartment 936A (e.g. see step S101 of FIG. 8). Thus, FIG. 7B shows the kit at time T=t1. The removed suctioned-lumened toothbrush device 1204A is used (e.g. see step S105 of FIG. 8) for a toothbrushing operation/session (e.g. using fluid from DD 1252) container—for example, in cooperation with base 100. For example, fluid for the toothbrushing operation/session may be loaded into reservoir 120 of base 100 according to the teachings of FIGS. 6A-6B and ejected (e.g. to deliver a stream of fluid into the patient's mouth during the toothbrushing operation/session) according to the teachings of FIGS. 6C-6D.

Before the toothbrushing or afterwards (e.g. at most 20 minutes before or at most 10 minutes before and/or at most 20 minutes after or at most 10 minutes after) the first counter 147A is manually incremented (e.g. by a nurse) from '0' to '1' (e.g. see step S109 of FIG. 8) indicating that one toothbrush operation has been performed or one operation using fluid DD has been formed. Thus, in FIG. 7B it is shown that: (i) the count-state of 147A is '1' and (ii) the count-state 147B is '0' (since no soft-tissue-lubrication operations and/or operations using fluid MM in container 1250 have been performed).

Figure 7B:
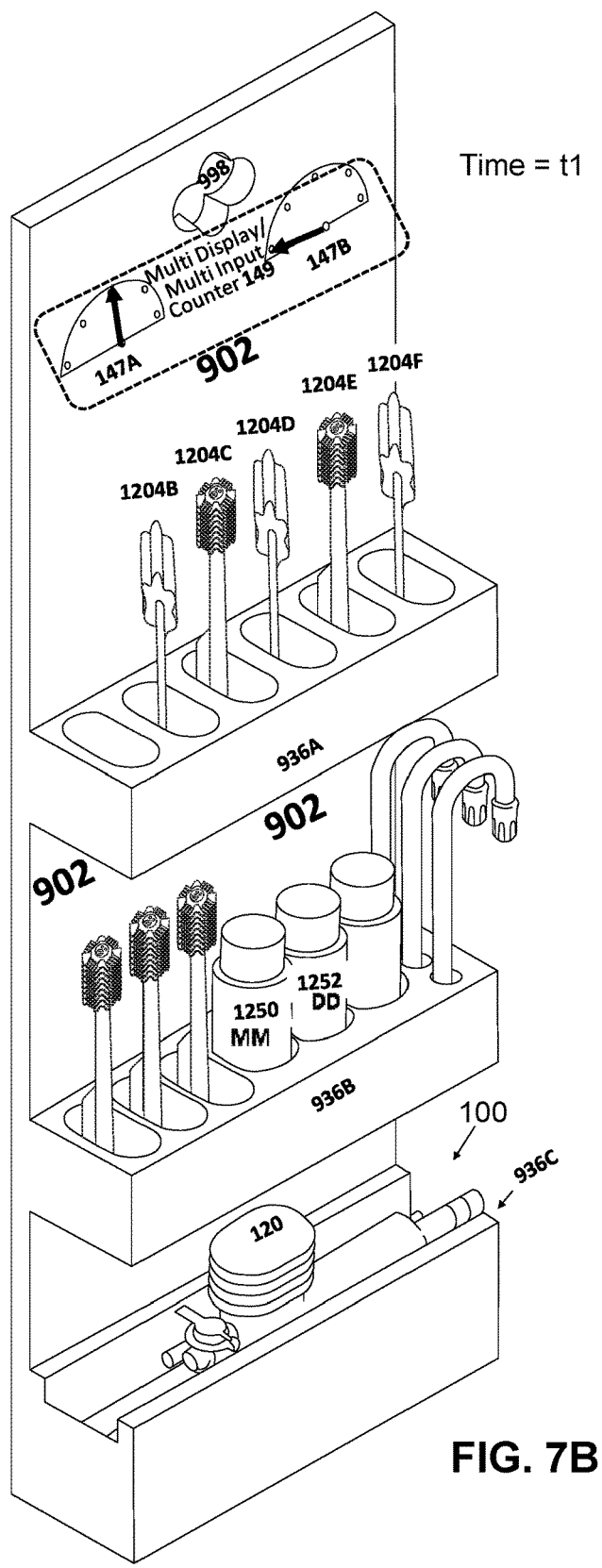
Figure 7C:
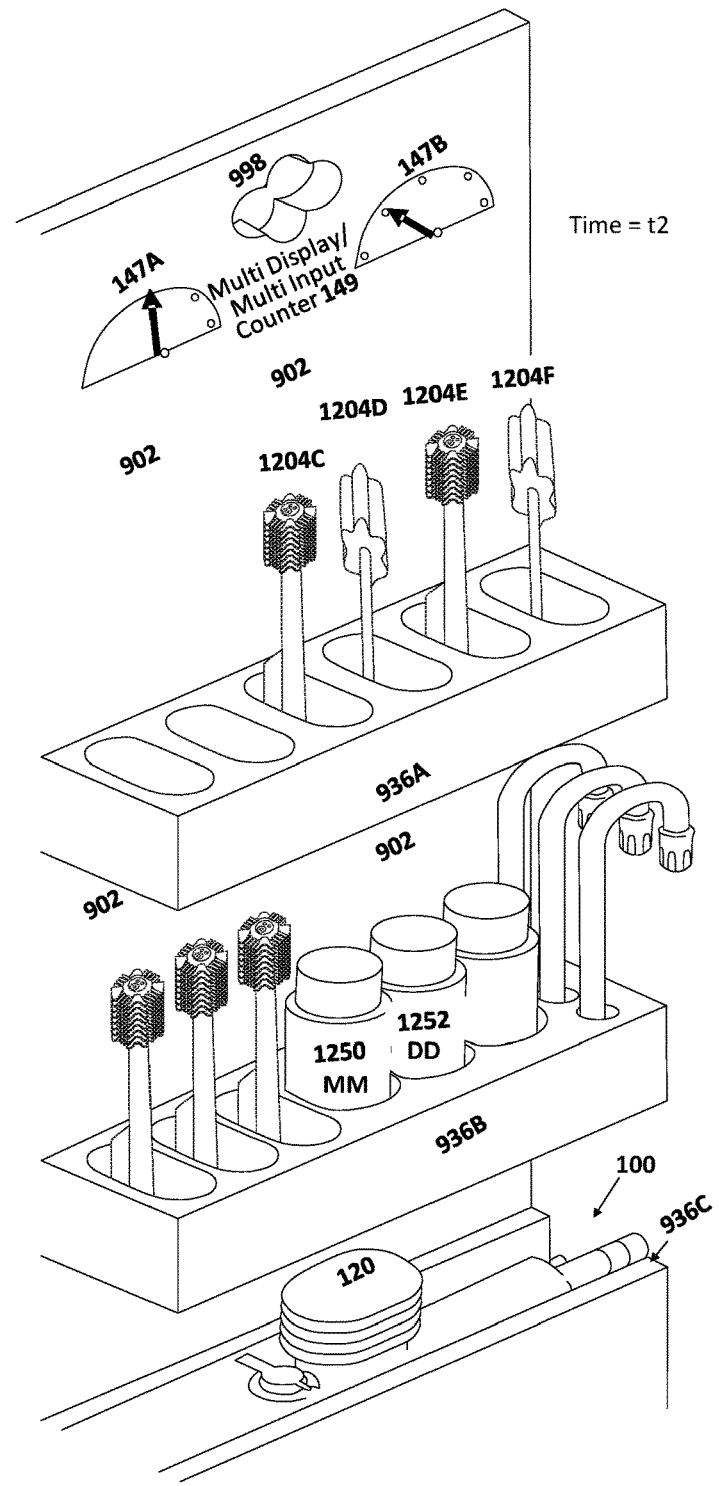

At a later time that is both after time T=t1 and before time T=t2, one of the sponged rod devices (1204B, 1204D or 1204F) is removed from compartment 936A (e.g. see step S113 of FIG. 8) and used for a soft-tissue lubrication session (e.g. see step S117 of FIG. 8). Before the soft-tissue lubrication operation or afterwards (e.g. at most 20 minutes before or at most 10 minutes before and/or at most 20 minutes after or at most 10 minutes after) the second counter 147B is manually incremented (e.g. by a nurse) from '0' to '1' (e.g. see step S121 of FIG. 8) indicating that one soft-tissue lubrication operations has been performed or one operation using fluid MM has been formed. Thus in FIG. 7C, (i) the count-state of element 147A is the same as shown in FIG. 7BN (i.e. still '1') since no toothbrushing operations were performed in the time interval between T=t1 and T=t2; and (ii) the count-state 147B of FIG. 7C is now '1' (since a soft-tissue lubrication operation—e.g. using fluid MM of container 1250 since a soft-tissue lubrication operation was performed in the time interval between T=t1 and T=t2). Someone walking through the ICU and viewing the kit can view the status of counter 149 and deduce that one of each types of operations (or operations using each type of fluid MM or DD) have been performed.

Figure 8:
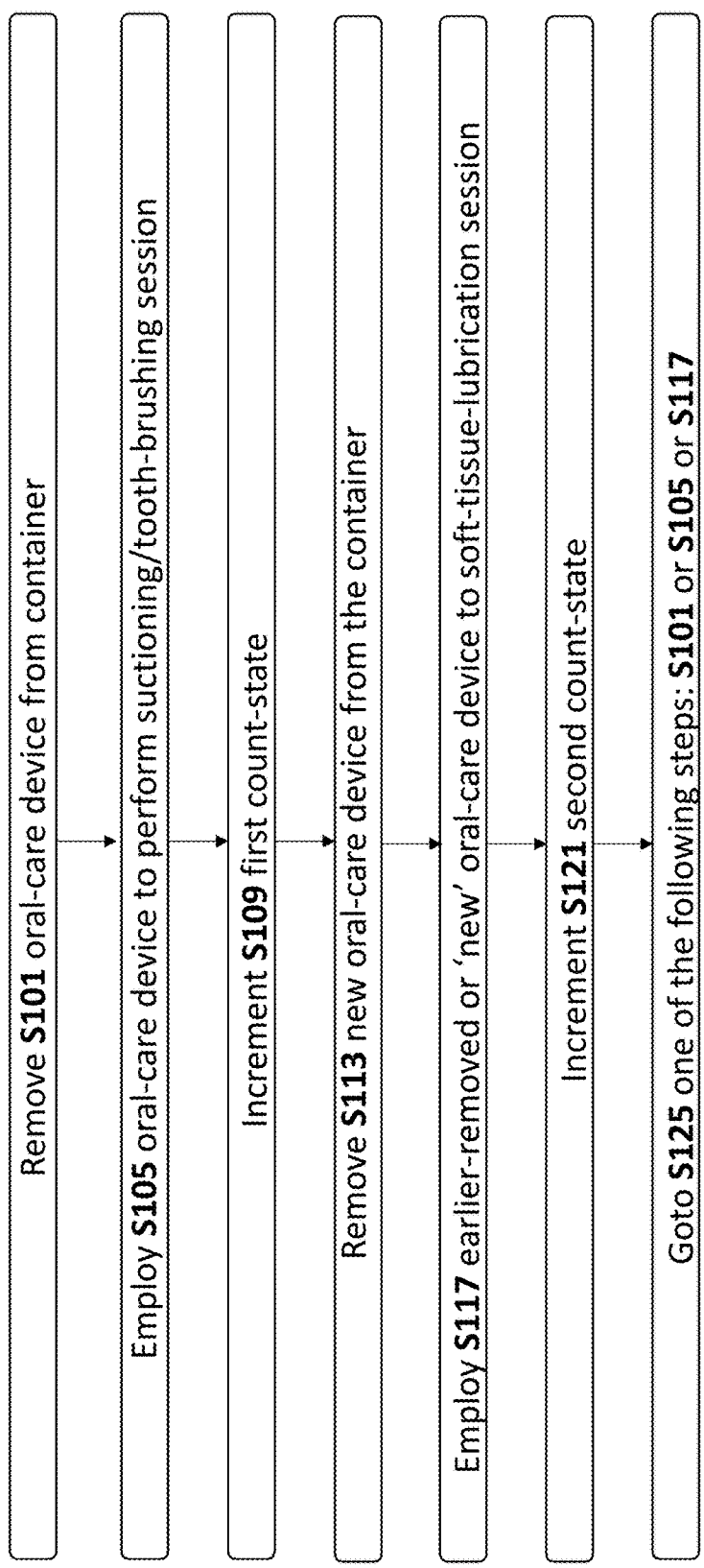
FIG. 8 is a flow-chart of an example method for using an oral care kit.

Also shown in FIG. 8 is step S125.

Figure 7D:
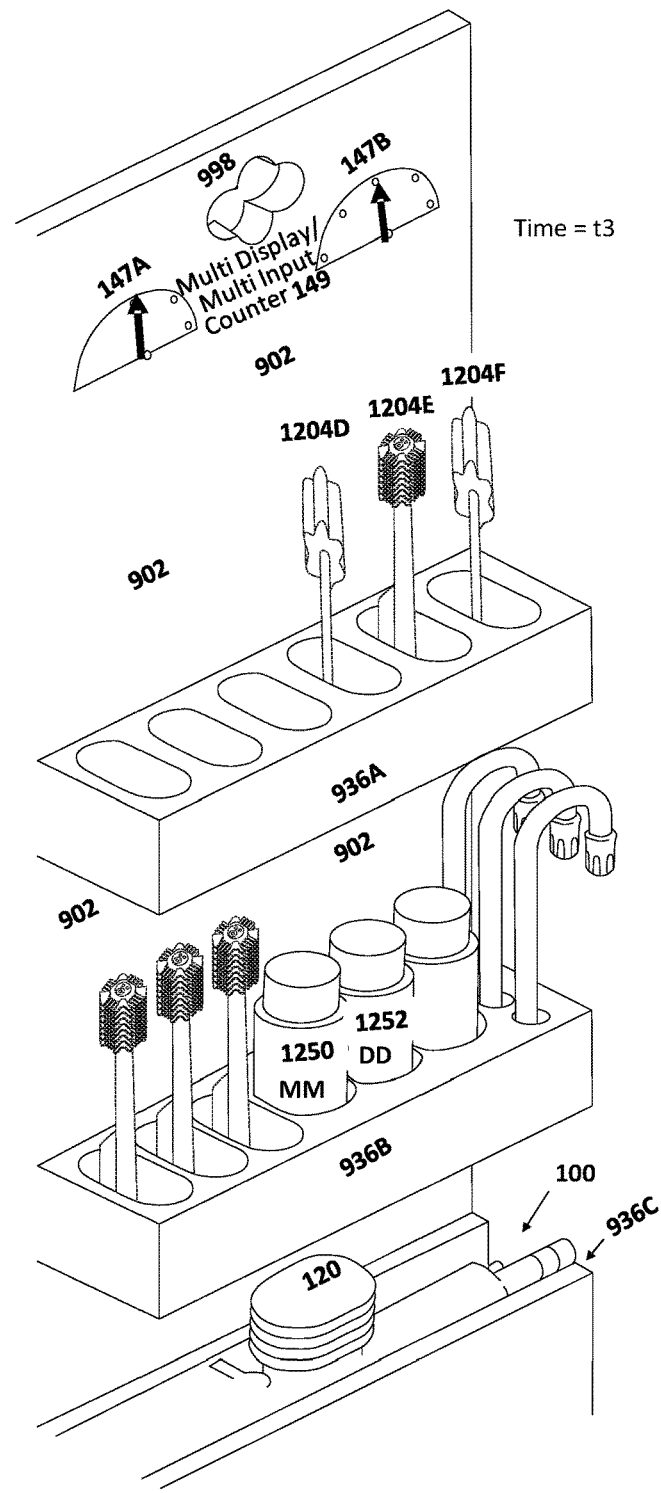
Figure 7E:
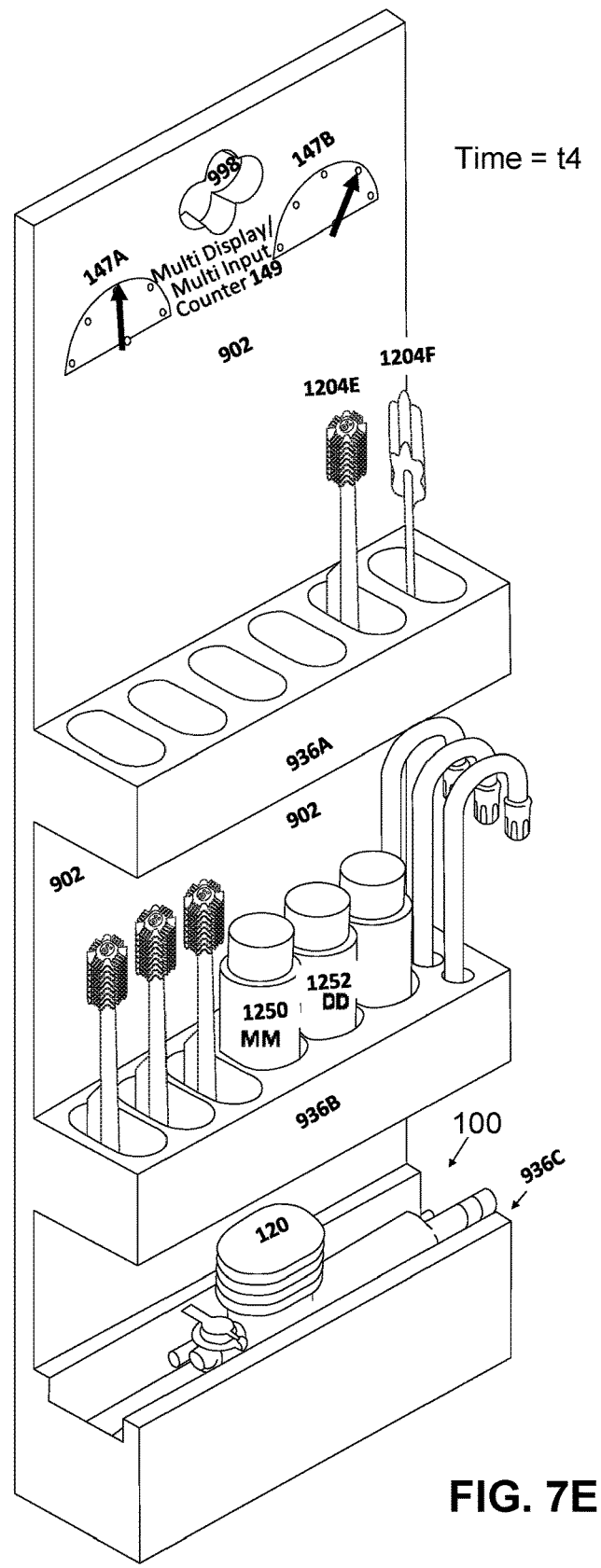
Figure 7F:
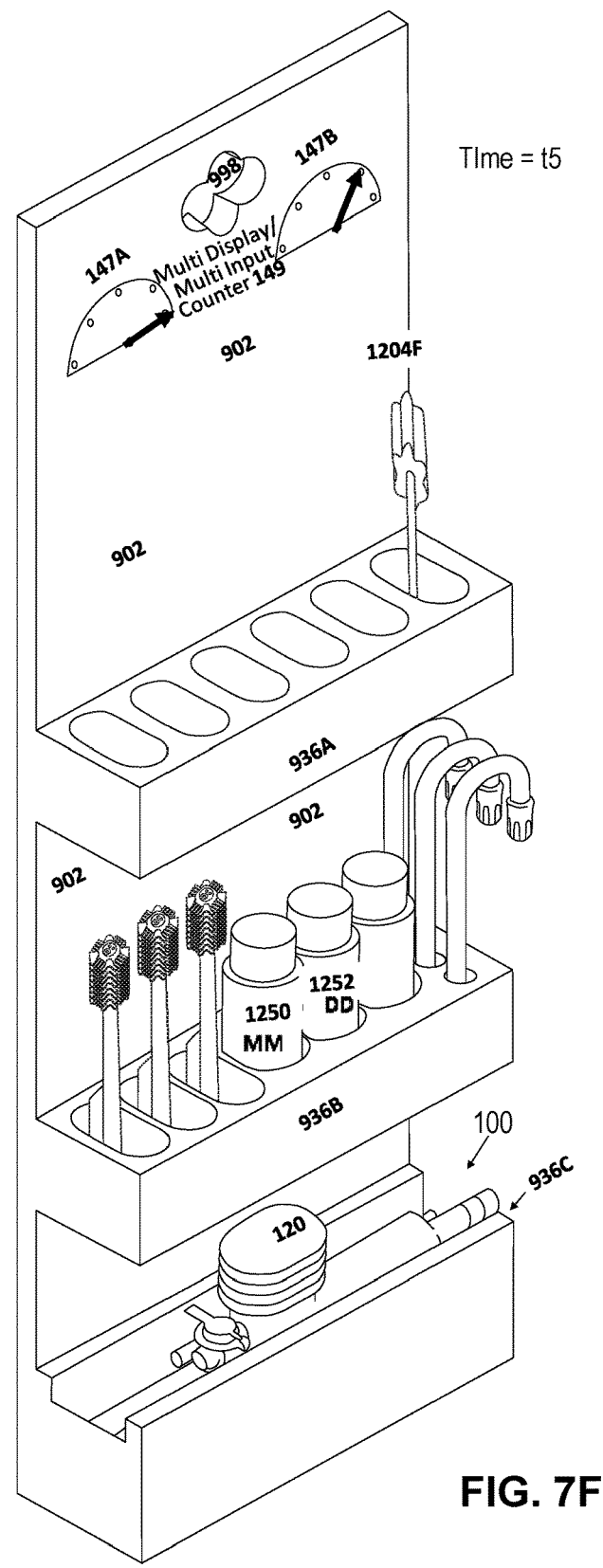

In the examples of FIGS. 7D-7F, toothbrushing operations (i.e. a count of which is tracked in 147A) and soft-tissue lubrication operations (i.e. a count of which is tracked in 147B) are performed alternately—thus, after T=t2 but before T=t3 a toothbrushing operation/session is performed, after T=t3 but before T=t4 a soft-tissue lubrication operation/session is performed, after T=t4 but before T=t5 a toothbrushing operation/session is performed.

One salient feature of the multi-input/multi-display counter 149 shown in FIG. 2 is that it is reversable (i.e. by rotating dial 146 or 145 in a counterclockwise direction) and resettable (e.g. from any state of FIGS. 7B-7F to the state of FIG. 7A). It is noted that the counter 149 includes single-input counters 147A and second 147B—other potential examples of single-input counters are shown in FIGS. 3C-3D, both of which are reversable and resettable.

A Discussion of Elements 777A-777C of FIG. 2A

As shown in FIG. 2, in some embodiments the kit and/or system comprises at least one or ar least two or at least three suction members—in FIG. 2A, three are shown—777A-777C are included in the kit and/or system.

In some embodiments, each suction member 777A-77C (e.g. without toothbrush bristles attached to the suction member) comprises a flexible tube having at least 90 degrees or at least 105 degrees or at least 120 degrees or at least 135 degrees or at least 150 degrees of bending freedom and capable of sustaining its bend angle without external sustaining forces—e.g. bending tube (e.g. rubber and/or plastic—biocompatible) comprising pliable (but not pliable) metal stiffening element (NOT SHOWN) disposed in an interior of the tube.

A Discussion of FIGS. 4A-4C and 5A-5B

FIGS. 4A-4C shows a multi-module toothbrush device comprising base 100 and head 150 modules when assembled. FIG. 4A emphasizes elements related to fluid delivery and FIGS. 4B-4C emphases elements related to suction.

FIGS. 5A-5B illustrate these modules in their unassembled state.

When used for toothbrushing, the assembled toothbrush device of FIG. 4A is capable of simultaneously performing three operations:
(I) a toothbrushing operating using toothbrush-bristle brush 165;
(II) a suctioning operation whereby matter (e.g. debris or biofilm) is suctioned into and through a suction lumen 170 [google]—in particular, the matter entered into lumen 170 via suction orifice 172 when (e.g. tapered) suction connector 171 is connected to source of negative pressure;
(III) a fluid-delivery operation whereby fluid stored within container 120 is expelled therefrom (e.g. according to the example of FIG. 6D), travels through fluid-delivery lumen 214 and exits therefrom via distal fluid delivery orifice 218.

Also visible in FIG. 5A is sheath 179—this element may be used in embodiments where the toothbrush is a 'power brush' where vibrations are transmitted from an electric motor (NOT SHOWN) in the base module 100 to the toothbrush 165 via a cavity 177 of sheath 179 which is part of head module 150.

Also illustrated in various figures is a longitudinal axis 196, a distal direction 192 and a proximal direction 194.

In some embodiments, a mechanical switch (NOT LABELLED) is provided—for example, the oral care device may include an electrical power brush, and switch serves to turn on or off the brush. As will be discussed below, in some embodiments head module base module comprises a distal-protruding portion of base module main body 110 within which a rotating eccentric mass (NOT SHOWN) causes vibrations which are transmitted to brush 165. For example, distal-producing portion may be received into a proximal-facing cavity of sheath element 179. Thus, sheath element 179 shown in FIG. 5A may be provided for power-brush embodiments. In other embodiments, the device functions as a 'manual toothbrush' with having no motor.

A Discussion of Fluid Loading/Unloading Mechanism (See FIGS. 6A-6D)

The onboard reservoir 120 of base module 100 is compressible and is in fluid communication with first 323 and second 324 one-way valves arranged in a specific manner relative to the onboard fluid reservoir 120. Use of the fluid loading/delivery mechanism is now explained according to a non-limiting example, where, a nurse (or other caregiver) holds the base module 100 in the palm of his/her hand, gripping with one or more fingers, and positioning his/her thumb on a surface of the reservoir.

Figure 6A:
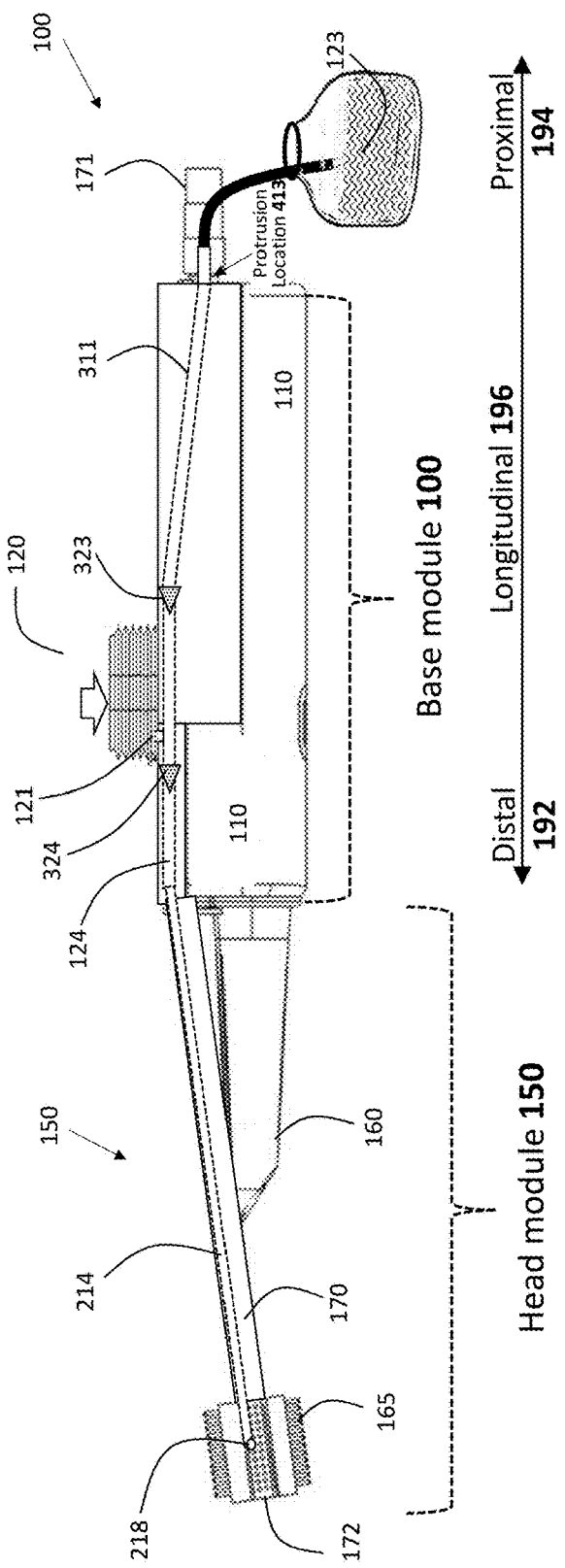
Figure 6B:
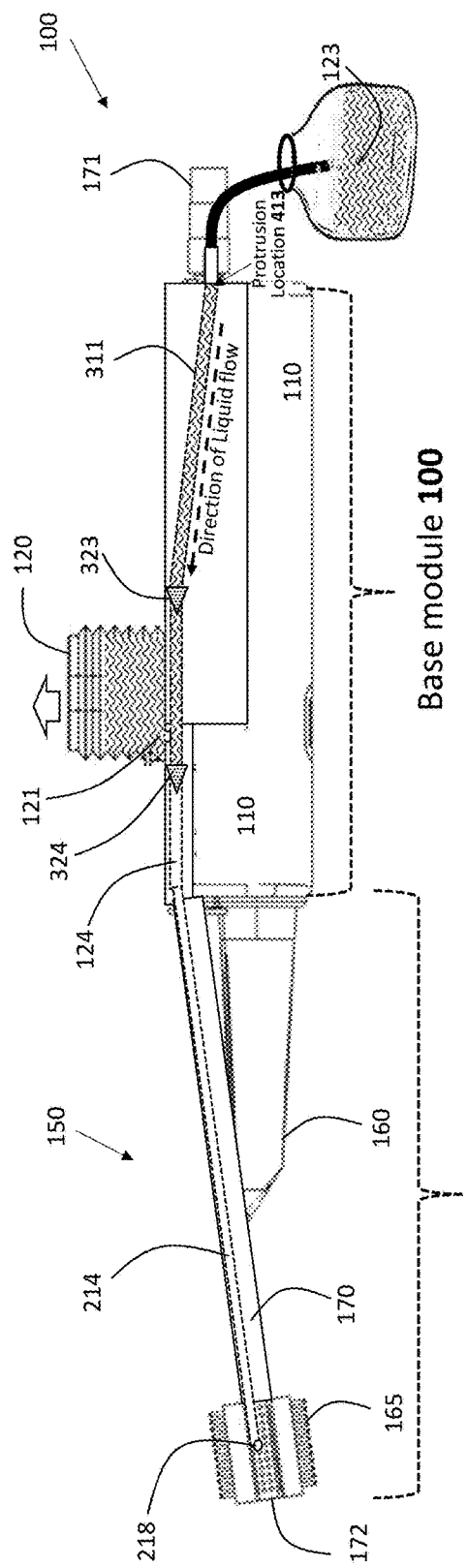
Figure 6D:
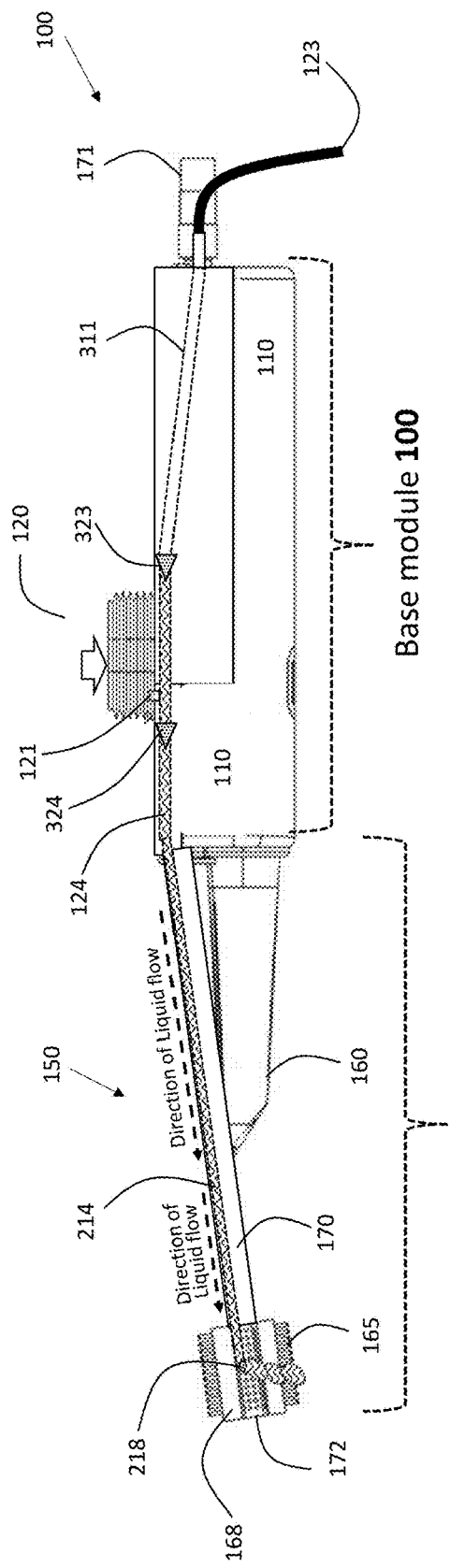

The prior to loading situation is shown in FIG. 6A—reservoir 120 is compressed and a proximal end 123 of inlet lumen 311 (i.e. proximal end 123 of the proximal tube portion 411 of inlet lumen 311) is immersed in fluid (e.g. fluid DD of container 1252).

According to this example and as shown in FIG. 6B, loading of the onboard compressive reservoir is performed as follows: after compressing the reservoir (i.e. as shown in FIG. 6A) by pre-applying pressure to the aforementioned reservoir surface with his/her thumb (e.g. in FIG. 6A), release of this thumb-applied pressure (e.g. in FIG. 6B) causes the compressible reservoir 120 to expand, generating negative pressure within the reservoir. This negative pressure suctions fluid (see FIG. 6B labelled as 'direction of liquid flow) through inlet tube or lumen 311, past the first one-way valve 323 and into the reservoir 120. During the fluid loading, a presence of the second one-way valve blocks backflow, via a section of the fluid-delivery lumen 124, into the fluid reservoir.

The loaded reservoir is shown in FIG. 6C which indicates the status before ejection of fluid.

According to this example, ejection of fluid (see FIG. 6D) from the onboard compressive reservoir 120 is performed as follows: the user simply re-applies pressure to the reservoir surface with his/her thumb, so as to force fluid out of the reservoir, though the fluid-delivery lumen section 124 and into the patient's mouth. This may be performed during a toothbrushing session (see step S105 of FIG. 8) when the base module 100 is coupled to the suction-lumened toothbrush head module 150 and the tip of the head module 150 (i.e. see the left side of head module 150—the distal end where distal suction orifice of suction lumen 170 is shown) is disposed within the patient's mouth.

As shown in FIG. 6D, the ejected fluid flows through the fluid lumen including the fluid delivery lumen section 214 of head module 150 and past the second one-way valve 324. During ejection, the first one-way valve 323 prevents fluid from passing back through the inlet tube towards a proximal end 123 of the inlet tube or lumen 311.

Bactericidal Effectiveness

For the present disclosure, a bactericidal effectiveness for our purpose is quantified by the measure of "minimum bactericidal concentrations" (MBC) and is Determined by in vitro test as described in—Comparison of the Antibacterial Properties of Three Mouthwashes Containing Chlorhexidine Against Oral Microbial Plaques: An in vitro Study.

Briefly summarized the test comprises the steps of: isolating colonies of *Streptococcus mutans*; tube dilution method is used for determining the minimum bactericidal concentrations (MBC).

A Brief Discussion of FIG. 9

In one particular example, at least some the toothbrush bristles are 'high-aspect-ratio-cross-section bristles' (see 'leaf' bristles of 946 of FIG. 9)—i.e. an aspect ratio of a cross section of the bristles exceeds at least 1.5 or at least 2 or at least 3 or at least 5—e.g. some leaf-bristles exhibit this characteristic.

In one particular example, a cross-section area of the bristle increases as one moves from the bottom of each bristle towards the top thereof.

In one particular example, the bristles are leaf-bristles'.

In some embodiments, and shown in FIG. 9 alternate stripes of leaf bristles 946 and conventional toothbrush bristles 948 are provided around a central axis of a suction lumen section of the suction-lumened-toothbrush.

In some examples (e.g. FIG. 9 which shows 'stripes' of leaf bristles), when pressurized fluid is forced to exit orifice 218 (e.g. pressurized fluid expelled from container 120— e.g. by applying pressure to container 120) the fluid leaves orifices in a location within the field of fluid-distribution elements or leaves which, for example, can serve to distribute the movement of the fluid so that fluid movement is not restricted to locations where a 'jet' of fluid leaves orifice 218. Thus, in some embodiments, there may be alternating 'stripes' (i.e. arranged lengthwise along the suction lumen 160) of a field 948 of toothbrush-bristles and field 946 of leaves where each leaf of at least a majority of leaves therein has an aspect ratio of at least 1.5 or at least 2 or at least 3 or at least 5 or at least 7.5 or at least 10).

In some embodiments, the toothbrush bristles and the leaf-field 946 are deployed at a distal end of the head module, the device further comprising a conical chamber that is sealed away from the suction lumen, the conical chamber being disposed at a proximal end of the head module and facing proximally, the conical chamber being sealed away from an interior of the suction lumen.

In the example of FIG. 9, orifice 218 is a fluid delivery orifice is located within a field 946 of fluid-distribution elements or 'leaves' which each have an aspect ratio (i.e. an aspect ratio of the cross section of each leaf where the 'cross section' is in the plane perpendicular to a central or elongate axis along a length of each fluid-distribution elements or leaves—the aspect ratio of each 'wide' leaf (e.g of a cross section thereof) may be at least 1.5 or at least 2 or at least 3 or at least 5 or at least 7.5 or at least 10).

The example of FIG. 9 shows 'stripes', when pressurized fluid is forced to exit orifice 218 (e.g. pressurized fluid expelled from container 120—e.g. by applying pressure to container 120) the fluid leaves orifices in a location within the field of fluid-distribution elements or leaves which, for example, can serve to distribute the movement of the fluid so that fluid movement is not restricted to locations where a 'jet' of fluid leaves orifice 218. Thus, in some embodiments, there may be alternating 'stripes' (i.e. arranged lengthwise along the suction lumen section 160) of a field 948 of toothbrush-bristles and field 946 of leaves (i.e. leaf bristles) where each leaf of at least a majority of leaves therein has an aspect ratio of at least 1.5 or at least 2 or at least 3 or at least 5 or at least 7.5 or at least 10).

A Brief Discussion of FIGS. 10A-10D, 11A-11B and 12A-12C

FIG. 10A illustrates an example where a proximal end of a proximal tube portion of an inlet lumen is immersed in (e.g. dipped in) a container of cleaning fluid before this fluid subsequently loaded form the container to an onboard reservoir of the base module.

FIG. 10B illustrates a device as fluid is expelled from the onboard reservoir of the base module.

Figure 10D:
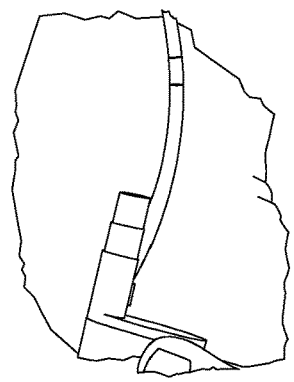
FIG. 10D is a closeup of the proximal tube portion for the example of FIG. 10B.
Figure 10C:
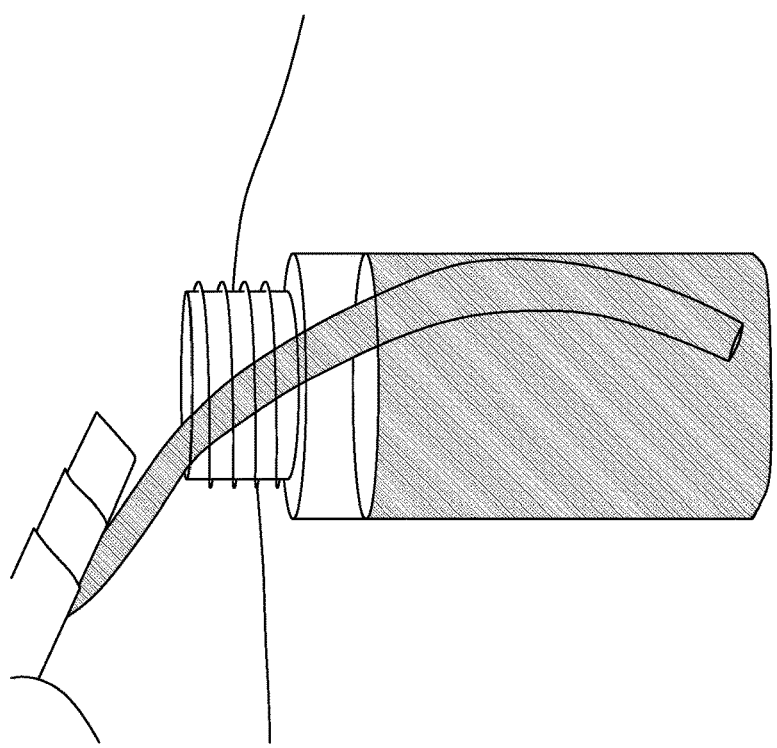
FIG. 10C is a closeup of the proximal tube portion within the container in the example of FIG. 10A.

FIG. 10C is a closeup of the proximal tube portion within the container in the example of FIG. 10A.

FIG. 10D is a closeup of the proximal tube portion for the example of FIG. 10B.

FIGS. 11A-11B illustrate the outline of the proximal tube portion respectively for the examples of FIGS. 10C-10D.

Figure 12C:
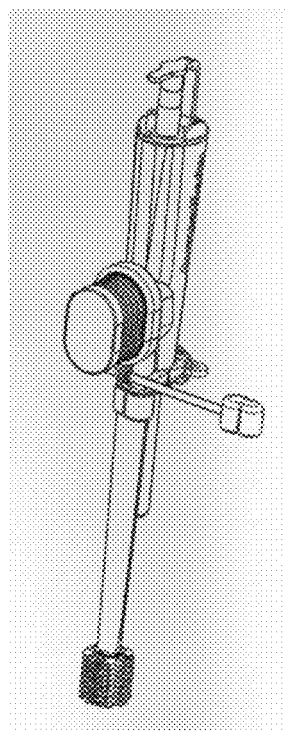
FIGS. 12A-12C show additional embodiments including at least one cap.
Figure 12A:
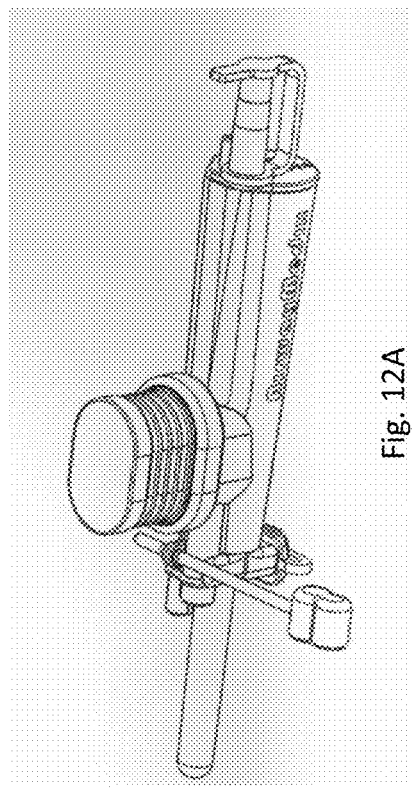
Figure 12B:
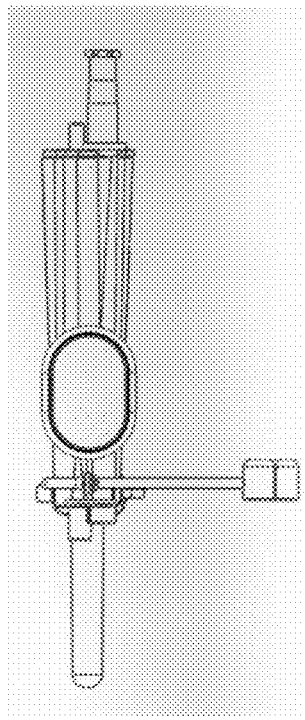

FIGS. 12A-12C show additional embodiments including at least one cap—e.g. for covering proximal connector 171.

Final Discussion

Embodiments of the present invention relate to systems, methods and kits for cleaning the oral cavity and/or teeth of a subject, including but not limited to an intubated subject.

The invention is herein described, by way of example only, with reference to the accompanying drawings. With specific reference now to the drawings in detail, it is stressed that the particulars shown are by way of example and for purposes of illustrative discussion of the preferred embodiments of the exemplary system only and are presented in the cause of providing what is believed to be a useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how several forms of the invention may be embodied in practice and how to make and use the embodiments.

For brevity, some explicit combinations of various features are not explicitly illustrated in the figures and/or described. It is now disclosed that any combination of the method or device features disclosed herein can be combined in any manner—including any combination of features—any combination of features can be included in any embodiment and/or omitted from any embodiments.

For the present disclosure, 'attachment' refers to direct or indirect attachment via attaching element(s) of the system or kit. When two modules are attached via an 'attachment element' the attachment element either be inherent to any of the modules (i.e. base, tail or head module) or could be an 'external element' that is external to the two modules and provided as part of a given system or kit. For example, the 'external element' may be part of a third module or may be any other external element. The external element may bridge between respective locations of each of the two attached modules. Examples of 'attachment elements' include but are not limited to fasteners, snaps, screw elements, spring-activated attachment elements, clamps, and magnetic attachment elements.

For the present disclosure, when a first module is 'distal' to a second module, that means the first module as a whole may be considered 'distal' to the second module, even if portions of the 'first' module are proximal to portions of the second module.

In some embodiments, the non-electronic multi-input/multi-display counter is reversable.

In some embodiments, the non-electronic multi-input/multi-display counter is resettable.

In some embodiments, the multi-input/multi-display counter the first and second user inputs and/or the first and second displays are attached to each other, e.g. distanced from each other by at most 50 cm or at most 40 cm or at most 30 cm or at most 20 cm or at most 10 cm at most 5 cm or at most 3 cm or at most 2 cm (e.g. the distance therebetween is fixed).

In some embodiments, the multi-input/multi-display counter a number of count states of the first and/or second user inputs is at least 2 or at least 3 or at least 4 or at least 5 and/or at most 10.

In some embodiments, the multi-input/multi-display counter the multi-input/multi-display counter is resettable (e.g. can be reset to a zero state) and/or reversible (e.g. after incrementing can be decremented) for one of both count-states thereof.

In some embodiments, the multi-input/multi-display counter the first user input is configured so that incrementing and/or decrementing the first count state does not induce motion of any of the rodded oral care-devices and/or of any liquid and/or of any fluid.

In some embodiments, the multi-input/multi-display counter the second user input is configured so that incrementing and/or decrementing the second count state does not induce motion of any of the rodded oral care-devices and/or of any liquid and/or of any fluid.

In some embodiments, the multi-input/multi-display counter the first and/or second user input is operated via rotation.

In some embodiments, the multi-input/multi-display counter the first and/or second user input is a slider and is operating by sliding a first element past a second element.

In some embodiments, the multi-input/multi-display counter the first and/or second user input is operated via rotation.

In some embodiments, the multi-input/multi-display counter the counter is configured such that the first and/or second count-states are symbolically displayed (i.e. by displaying a different symbol for each count-states—e.g. alpha-numerical symbol or numerical symbol).

In some embodiments, wherein the multi-input/multi-display counter is hanging, either whole or in pieces (e.g. an entirety of the multi-input/multi-display counter is hanging via a single, as it is employed to track the numbers of distinct toothbrushing sessions and distinct oral-soft-tissue-lubricating sessions.

In some embodiments, both the first and second user inputs and/or both of the first and second displays are attached to each other via a common hanger.

In some embodiments, at least one or at least some or at least all of the rodded-oral care devices, before use in a respective oral care session, are stored on a first support element that hangs from a hanger that is common to the first and/or second user inputs of the multi-input/multi-display counter and removed from the support element before the oral care session.

In some embodiments, the support element is selected from the group consisting of a shelf and a bag (e.g. resalable bag).

In some embodiments, the support element is a pop-up support element.

In some embodiments, the multi-input/multi-display counter is mounted to a substrate board and hanged from a hanging element thereof or attached thereto, and wherein the support element is mounted to and/or hanging from and/or attached to the substrate board.

In some embodiments, wherein (i) the oral-care sessions are performed to the human subject when the subject is lying down on a bed, and the multi-input/multi-display counter (and/or the first or second input thereof) are hanging at a bedside location and/or within 10 meters of the bed and/or (ii) the first user input and/or second user input is(are) employed to increment the first and/or second count states when the multi-input/multi-display counter (and/or the first or second input thereof) are hanging at a bedside location and/or within 10 meters of the bed.

In some embodiments, further comprising before performing the oral-care sessions, populating, with at least one or at least two or at least majority of rodded oral care devices used to perform the oral care sessions, a hanging support element that is hanging via a hanging element, such that at the time of population, both the support element and at least one user input (or an entirety of) the multi-input/multi-display counter is having via the same hanging element of the populated support element.

In some embodiments, the oral-care sessions are performed to the human subject when the subject is lying down on a bed, and the hanging support element hangs at a bedside location and/or within 10 meters of the bed.

In some embodiments, at least one or the oral care sessions (e.g. of the 'first type') are performed by delivering pressurized fluid from a fluid pump and via a side-facing fluid-delivery orifice(s) 218 so that pressurized fluid delivered therethrough lubricates the subject's gum(s) and wherein the fluid pump is stored on the first support element or on a second support element attached thereto so that the fluid-pump-supporting support element hangs from a hanger that is common to the first and/or second user inputs of the multi-input/multi-display counter and removed from the support element before the oral care session.

In some embodiments, each of at least one or at least two or at least a majority of or all of the rodded oral care devices reside are packaged within a sealed package within which no fluid is stored (e.g. at most one rodded oral care devices per package, between 1-2 rodded oral care devices per package, at most 5 or at most 4 or at most 3 or at most 2 rodded oral care devices per package).

In some embodiments, the multi-input/multi-display counter is such that each count statute is simultaneously visible (e.g. as opposed to toggling).

In some embodiments, the multi-input/multi-display counter continuously displays the state of both counters simultaneously for at least 1 day or at least 1 week or at least 2 weeks or at least 3 weeks.

In some embodiments, the multi-input/multi-display counter is permanently in a display mode to permanently display any value of the first count-state and any vale of the second count-state.

In some embodiments, any method disclosed herein may be performed using any kit disclosed herein. (e.g. after morning setup there is no moisturizing event before a brushing event (e.g. there is no 'streak' of brushing events that is not 'broken' by a moisturizing event in the interim.) (e.g. at least 4 hours between brushing sessions).

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the present disclosure has been described with respect to various specific embodiments presented thereof for the sake of illustration only, such specifically disclosed embodiments should not be considered limiting. Many other alternatives, modifications and variations of such embodiments will occur to those skilled in the art based upon Applicant's disclosure herein. Accordingly, it is intended to embrace all such alternatives, modifications and variations and to be bound only by the spirit and scope of the appended claims and any change which come within their meaning and range of equivalency.

In the description and claims of the present disclosure, each of the verbs "comprise", "include" and "have", and conjugates thereof, are used to indicate that the object or objects of the verb are not necessarily a complete listing of features, members, steps, components, elements or parts of the subject or subjects of the verb.

As used herein, the singular form "a", "an" and "the" include plural references and mean "at least one" or "one or more" unless the context clearly dictates otherwise.

Unless otherwise stated, the use of the expression "and/or" between the last two members of a list of options for selection indicates that a selection of one or more of the listed options is appropriate and may be made.

Unless otherwise stated, adjectives such as "substantially" and "about" that modify a condition or relationship characteristic of a feature or features of an embodiment of the present technology, are to be understood to mean that the condition or characteristic is defined to within tolerances that are acceptable for operation of the embodiment for an application for which it is intended.

To the extent necessary to understand or complete the present disclosure, all publications, patents, and patent applications mentioned herein, including in particular the applications of the Applicant, are expressly incorporated by reference in their entirety by reference as is fully set forth herein.

What is claimed is:

1. An oral care kit comprising:
   a. a base module comprising:
      i. an onboard compressible fluid reservoir having an equilibrium size so that, when released from a compressed configuration, a restoration force urges size-increase of the reservoir back to the equilibrium size;
      ii. an onboard inlet lumen comprising a proximal tube portion that:
         A. protrudes from a main body of the base module; and
         B. has a proximal opening,
         the inlet lumen providing fluid communication between the proximal opening of the proximal tube portion and the compressible fluid reservoir for loading thereof;
      iii. a first one-way valve disposed between the proximal opening of the proximal tube portion of the inlet lumen and the compressible fluid reservoir so as to permit fluid inflow past the first one-way valve towards the fluid reservoir and to block fluid back-flow from the reservoir in the opposite direction;
      iv. a base-module-onboard fluid-delivery lumen section;
      v. a second one-way valve disposed in the onboard fluid-delivery lumen section to permit fluid outflow from the reservoir past the second one-way valve and to block fluid backflow towards the reservoir in the opposite direction;
      vi. a base-module onboard suction lumen section that does not lead into the fluid compressible reservoir;
   b. a plurality of rodded oral care devices, at least one of which is a suction-lumened-toothbrush including an head-module onboard suction lumen section, an onboard fluid-delivery-lumen section having a fluid-delivery-orifice at a distal end of the head-module-onboard fluid-delivery-lumen section, and a plurality of toothbrush bristles;
   c. a hanger;
   d. a support element that hangs from the hanger, the support element for supporting each rodded oral care device of the plurality of devices; and
   e. a non-electronic multi-input multi-display counter attached to and supported by the hanger the multi-input multi-display counter independently displaying first and second count-states, the multi-input multi-display counter including first and second independently-operable user inputs respectively associated with the first and second count states such that:
      (I) in response to user engagement of the first user input, the first count state is incremented or decremented; and
      (II) in response to user engagement of the second user input, the second count state is incremented or decremented,
   wherein:
      i. the suction-lumened toothbrush is detachably attachable to the base module to form an oral care device so that upon attachment:
         A. the respective suction lumen sections form a continuous suction lumen along a length of oral care device; and
         B. the respective fluid-delivery sections form a continuous fluid-delivery lumen that provides fluid communication between an interior of the fluid reservoir and the fluid-delivery orifice;
      ii. after attachment, expansion of the fluid reservoir from an at-least partially compressed configuration loads the fluid reservoir so that a negative pressure created within the expanding reservoir suctions fluid past the first one-way valve into the fluid reservoir while a presence of the second one-way valve blocks back-flow through the base-module-onboard fluid-delivery lumen section and into the fluid reservoir;
      iii. after attachment and after loading, compression of the fluid reservoir unloads the fluid reservoir to force the unloaded fluid to exit the fluid-delivery orifice so that outflow from the fluid reservoir flows through the continuous fluid-delivery lumen formed by the attachment and past the second one-way valve while a presence of the first one-way valve prevents flow of fluid from passing back towards proximal opening of the inlet lumen.

2. The oral care kit of claim 1 wherein the support element is a bag, slot or a shelf.

3. The oral care kit of claim 1 wherein:
   i. a motor resides on the base module;
   ii. the base-module-residing motor drives rotational and/or vibrational motion of the toothbrush bristles when the suction-lumened toothbrush is attached to the base module.

4. The oral care kit of claim 1, lacking a motor, where the brush is operated only manually.

5. The kit of claim 1, wherein alternate stripes of leaf bristles and conventional toothbrush bristles are provided around a central axis of the head-module onboard suction lumen section of the suction-lumened-toothbrush.

6. The kit of claim 1, wherein the non-electronic multi-input multi-display counter is reversable.

7. The kit of claim 1, wherein the non-electronic multi-input multi-display counter is resettable.

8. A method comprising assembling a system for oral care, the method comprising:
   a. providing the kit of claim 1; and
   b. disposing element of the kit of claim 1 so that:
      i. the support element hangs via the hanger;
      ii. The support element holds both the base module and all oral care device of the plurality of oral care devices; and
      iii. the non-electronic multi-input multi-display counter, the base module and all oral care devices of the plurality of oral care devices are simultaneously supports by the hanger.

9. The method of claim 8 further comprising subsequent to the kit assembly, incrementing the first user input of the multi-input multi-display counter to track a number of toothbrushing operations performed by the oral care devices distinct toothbrushing sessions and a number of distinct oral-soft-tissue lubricating oral-tissue-lubricating sessions performed by the rodded oral care devices.

10. The method of claim 9 wherein at least one of the distinct toothbrushing sessions are performed by the combination of the base module and the suction-lumened-toothbrush when attached to each other.

11. The method of claim 8 further comprising the step of attaching the base module to the suction-lumened-toothbrush so that:
   A. the respective suction lumen sections form the continuous suction lumen along a length of oral care device;

B. the respective fluid-delivery sections form the continuous fluid-delivery lumen that provides fluid communication between an interior of the fluid reservoir and the fluid-delivery orifice.

\* \* \* \* \*